United States Patent
Kim et al.

(10) Patent No.: US 11,676,724 B1
(45) Date of Patent: Jun. 13, 2023

(54) METHOD OF CALCULATING DIAGNOSTIC SCORE FOR PROSTATE CANCER AND USE THEREOF

(71) Applicant: Urotech. Co., Ltd., Cheongju-Si (KR)

(72) Inventors: Wun Jae Kim, Seoul (KR); Pil Du Jeong, Cheongju-Si (KR)

(73) Assignee: Urotech. Co., Ltd., Cheongju-Si (KR)

( * ) Notice: Subject to any disclaimer, the term of this patent is extended or adjusted under 35 U.S.C. 154(b) by 0 days.

(21) Appl. No.: 17/318,588

(22) Filed: May 12, 2021

(30) Foreign Application Priority Data

Sep. 8, 2020 (KR) .................. 10-2020-0114964

(51) Int. Cl.
G16H 50/20 (2018.01)
C12Q 1/6886 (2018.01)
G16H 10/40 (2018.01)
G16H 50/70 (2018.01)
G16H 50/30 (2018.01)
G16H 10/60 (2018.01)

(52) U.S. Cl.
CPC ........... *G16H 50/20* (2018.01); *C12Q 1/6886* (2013.01); *G16H 10/40* (2018.01); *G16H 10/60* (2018.01); *G16H 50/30* (2018.01); *G16H 50/70* (2018.01); *C12Q 2600/178* (2013.01)

(58) Field of Classification Search
CPC ........ G16H 50/20; G16H 10/40; G16H 10/60; G16H 50/30; G16H 50/70; C12Q 1/6886; C12Q 2600/178
See application file for complete search history.

(56) References Cited

U.S. PATENT DOCUMENTS

2017/0121779 A1 5/2017 Kondou et al.
2020/0199688 A1* 6/2020 Kondou .................. C12M 1/00

FOREIGN PATENT DOCUMENTS

| KR | 20150023904 A | 3/2015 |
| KR | 20160006673 A | 1/2016 |
| KR | 2019/0110834 A | 10/2019 |
| KR | 20190113814 A | 10/2019 |
| KR | 102052398 B1 | 12/2019 |
| WO | WO-2019175786 A1 | 9/2019 |

OTHER PUBLICATIONS

Fredsoe et al., "Diagnostic and Prognostic MicroRNA Biomarkers for Prostate Cancer in Cell-free Urine," European Urology Focus, 4: 825-833 (2018).
Notice of Allowance for KR Application No. 10-2020-0114964 dated Nov. 10, 2022 w/English Translation.
International Search Report and Written Opinion for Application No. PCT/KR2020/012128 dated Jun. 2, 2021.

* cited by examiner

*Primary Examiner* — Jerry Lin
(74) *Attorney, Agent, or Firm* — Foley Hoag LLP

(57) ABSTRACT

The present specification provides a method of calculating a diagnostic score for prostate cancer by combining at least two values. The method comprises preparing a sample, obtaining a first value, obtaining a second value, and calculating a diagnostic score. The sample is a urine sample from a subject, and the first value corresponds to an amount of a hsa-miR-3659 or hsa-miR-3679-5p derived from extracellular vesicles in the sample, and the second value corresponds to a miRNA derived from the extracellular vesicles in the sample. Both the first and second values include information on whether the subject has developed prostate cancer, and the second value corresponds to a normalization factor specialized for the first value. The diagnostic score for prostate cancer calculated according to the method is characterized by being capable of diagnosing prostate cancer. The present specification provides a use of the diagnostic score for prostate cancer.

6 Claims, 19 Drawing Sheets

Specification includes a Sequence Listing.

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Primer sequence for hsa-miR-3659

<400> SEQUENCE: 1
tgagtgttgt ctacgagggc a                                          21

<210> SEQ ID NO 2
<211> LENGTH: 23
<212> TYPE: DNA
<213> ORGANISM: Artificial Sequence
<220> FEATURE:
<223> OTHER INFORMATION: Primer sequence for hsa-miR-3679-5p

<400> SEQUENCE: 2
tgaggatatg gcagggaagg gga                                        23

<210> SEQ ID NO 3
<211> LENGTH: 20
<212> TYPE: DNA
<213> ORGANISM: Artificial Sequence
<220> FEATURE:
<223> OTHER INFORMATION: Primer sequence for hsv2-miR-H9

<400> SEQUENCE: 3
ctcggaggtg gagtcgcggt                                            20

<210> SEQ ID NO 4
<211> LENGTH: 23
<212> TYPE: DNA
<213> ORGANISM: Artificial Sequence
<220> FEATURE:
<223> OTHER INFORMATION: Primer sequence for hsv1-miR-H18
```

-continued

```
<400> SEQUENCE: 4
cccgcccgcc ggacgccggg acc                                          23

<210> SEQ ID NO 5
<211> LENGTH: 22
<212> TYPE: DNA
<213> ORGANISM: Artificial Sequence
<220> FEATURE:
<223> OTHER INFORMATION: Primer sequence for hsa-miR-1913

<400> SEQUENCE: 5
tctgccccct ccgctgctgc ca                                           22

<210> SEQ ID NO 6
<211> LENGTH: 22
<212> TYPE: DNA
<213> ORGANISM: Artificial Sequence
<220> FEATURE:
<223> OTHER INFORMATION: Primer sequence for hsa-miR-30a-5p

<400> SEQUENCE: 6
tgtaaacatc ctcgactgga ag                                           22

<210> SEQ ID NO 7
<211> LENGTH: 23
<212> TYPE: DNA
<213> ORGANISM: Artificial Sequence
<220> FEATURE:
<223> OTHER INFORMATION: Primer sequence for hsa-miR-30c-5p

<400> SEQUENCE: 7
tgtaaacatc ctacactctc agc                                          23

<210> SEQ ID NO 8
<211> LENGTH: 21
<212> TYPE: DNA
<213> ORGANISM: Artificial Sequence
<220> FEATURE:
<223> OTHER INFORMATION: Primer sequence for hsa-miR-31-5p

<400> SEQUENCE: 8
aggcaagatg ctggcatagc t                                            21
```

METHOD OF CALCULATING DIAGNOSTIC SCORE FOR PROSTATE CANCER AND USE THEREOF

CROSS-REFERENCE TO RELATED APPLICATION

This application claims priority to and the benefit of Korean Patent Application No. 10-2020-0114964, filed on Sep. 8, 2020, the disclosure of which is incorporated herein by reference in its entirety.

SEQUENCE LISTING

The instant application contains a Sequence Listing which has been submitted electronically in ASCII format and is hereby incorporated by reference in its entirety. Said ASCII copy, created on May 12, 2021, is named IPH-00301_SL.txt and is 1,964 bytes in size.

BACKGROUND OF THE INVENTION

Technical Field

The present invention relates to technology regarding a method for calculating a diagnostic score capable of providing an information on diagnosis of the onset of prostate cancer by measuring an expression level of a biomarker included in a subject's urine.

Background Art

In principle, a standard method of diagnosing prostate cancer is a biopsy in which a small amount of prostate tissue is collected from a subject and then the development of cancer cells is determined. However, the biopsy involves a very painful process for a subject. Therefore, it is undesirable to perform the biopsy only because the subject shows symptoms suspected of the onset of prostate cancer (for example, urinary symptoms such as polyuria, urodynia, and the like). Thus, when the subject shows symptoms suspected of the onset of prostate cancer, it is common to take a body fluid (for example, blood or urine) from the subject, perform an indirect examination for the onset of prostate cancer, and then determine whether a biopsy is required based on these results. Currently, in clinical practice, a prostate-specific antigen (PSA) test is typically carried out by taking blood from a subject to measure a concentration of PSA in a blood sample. However, because the PSA test is controversial regarding its accuracy and diagnostic ability, there is a need for development of a reliable method of non-invasively diagnosing prostate cancer.

BRIEF SUMMARY OF THE INVENTION

Technical Problem

One aspect of the present invention is to provide a method of calculating a diagnostic score capable of providing information on whether a subject has developed prostate cancer.

Another aspect of the present invention is to provide a method of determining diagnostic criteria for diagnosis of prostate cancer from the diagnostic score.

Still another aspect of the present invention is to provide a method of providing information on the diagnosis of prostate cancer from the diagnostic score.

Technical Solution

According to the present specification, a method of calculating a diagnostic score for prostate cancer by combining at least two values is provided. The method comprises: preparing a sample of a subject, wherein the sample is a urine sample; obtaining a first value being related to an amount of a first target in the sample, wherein the first target is hsa-miR-3659 or hsa-miR-3679 derived from extracellular vesicles in the sample, wherein the first value reflects a first information having ability to diagnose the prostate cancer of the subject, however, the first value itself cannot be used alone to diagnose the prostate cancer of the subject, since the first value also reflects a first noise simultaneously with the first information, wherein the first noise is caused by an endogenous factor being independent from a factor related to the prostate cancer; obtaining a second value being related to an amount of a second target in the sample; wherein the second target is a miRNA derived from the extracellular vesicles in the sample, wherein the second value reflects a second information being related to whether the subject is be with the prostate cancer, wherein the second value reflects a third information being related to the endogenous factor, wherein the third information is significantly correlated with the first noise, whereby the first noise being reflected in the first value can be controlled by using the second value; and calculating the diagnostic score for the prostate cancer by using the first value and the second value, whereby the diagnostic score can be used to diagnose prostate cancer.

In one embodiment, the second target is hsv2-miR-H9-5p or hsa-miR-1913.

In one embodiment, the diagnostic score is calculated by a ratio of the first value and the second value.

In one embodiment, the endogenous factor comprises: a first condition associated with the sample; and a second condition associated with the subject.

In one embodiment, the first condition comprises one or more selected from the group consisting of an amount of the sample, a sample collection time, a method of collecting a sample, a sample storage duration, a sample storage temperature, and a method of subdividing a sample.

In one embodiment, the second condition comprises one or more selected from the group consisting of a gender of the subject, an age of the subject, a race of the subject, a weight of the subject, a renal function of the subject, a hydration state of the subject.

In one embodiment, the obtaining of the first value further comprises: synthesizing first cDNA of the first target in the sample; amplifying the first cDNA by a polymerase chain reaction using a first primer, wherein the first primer is selected from the group consisting of SEQ ID NOs: 1 to 2; and determining the first value from the amplification results of the first cDNA.

In one embodiment, the obtaining of the second value may further include: synthesizing second cDNA of the second target in the sample; amplifying the second cDNA by a polymerase chain reaction using a second primer, wherein the second primer has a sequence having homology to a sequence of the second target or a sequence capable of complementarily binding to the sequence of the second target; and determining the second value from the amplification results of the second cDNA.

In one embodiment, the second target may be hsv2-miR-H9-5p or hsa-miR-1913, and the second primer may be selected from the group consisting of SEQ ID NOs: 3 and 5.

According to the present specification, a method of determining diagnostic criteria for diagnosis for prostate cancer is provided. The method comprises: obtaining a first data set, wherein the first data set includes a list of whether each subject in a cohort has developed prostate cancer, and a list of diagnostic scores calculated for each subject in the cohort according to the method of calculating a diagnostic score for prostate cancer, wherein the cohort comprises at least one subject who is normal or has developed benign prostatic hyperplasia, and at least one subject who has developed prostate cancer; and determining the diagnostic criteria for diagnosis of prostate cancer from the first data set.

In one embodiment, the diagnostic criteria comprises single values having the same dimension as the diagnostic scores.

In one embodiment, the diagnostic criteria comprises one or more probability values of developing prostate cancer.

According to the present specification, a method of providing information on the diagnosis of the onset of prostate cancer in a subject is provided. The method comprises: calculating a diagnostic score for prostate cancer in the subject according to the method of calculating a diagnostic score; and determining a risk factor from the diagnostic score for prostate cancer with reference to at least one predetermined value.

In one embodiment, the predetermined value is the diagnostic criteria determined according to the method of determining diagnostic criteria.

Advantageous Effects

Information for non-invasive diagnosis of prostate cancer from a urine sample of a subject can be provided using the method of calculating a diagnostic score provided herein.

BRIEF DESCRIPTION OF THE DRAWINGS

FIG. 2A shows results of Example 1 (hsv2-miR-H9 to hsa-miR-3659). FIG. 2B shows results of Example 2 (hsa-miR-1913 to hsa-miR-3659).

FIG. 3A shows results of Example 3 (hsv2-miR-H9 to hsa-miR-3679-5p). FIG. 3B shows results of Example 4 (hsa-miR-1913 to hsa-miR-3679-5p).

FIG. 4A shows results of Example 5 (hsv1-miR-H18 to hsa-miR-3659). FIG. 4B shows results of Example 6 (hsv1-miR-H18 to hsa-miR-3679-5p).

FIG. 5A shows results of Comparative Example 1 (hsa-miR-30a-5p to hsa-miR-31-5p) FIG. 5B shows results of Comparative Example 2 (hsa-miR-30c-5p to hsa-miR-31-5p).

FIG. 6A shows results of Example 1 (hsv2-miR-H9 to hsa-miR-3659). FIG. 6B shows results of Example 2 (hsa-miR-1913 to hsa-miR-3659).

FIG. 7A shows results of Example 3 (hsv2-miR-H9 to hsa-miR-3679-5p). FIG. 7B shows results of Example 4 (hsa-miR-1913 to hsa-miR-3679-5p).

FIG. 8A shows results of Example 5 (hsv1-miR-H18 to hsa-miR-3659). FIG. 8B shows results of Example 6 (hsv1-miR-H18 to hsa-miR-3679-5p).

FIG. 9A shows results of Comparative Example 1 (hsa-miR-30a-5p to hsa-miR-31-5p). FIG. 9B shows results of Comparative Example 2 (hsa-miR-30c-5p to hsa-miR-31-5p).

FIG. 11A shows an ROC curve for Example 1 (hsv2-miR-H9 to hsa-miR-3659). FIG. 11B shows an ROC curve for Example 2 (hsa-miR-1913 to hsa-miR-3659).

FIG. 12A shows an ROC curve for Example 3 (hsv2-miR-H9 to hsa-miR-3679-5p). FIG. 12B shows an ROC curve for Example 4 (hsa-miR-1913 to hsa-miR-3679-5p).

FIG. 13A shows an ROC curve for Example 5 (hsv1-miR-H18 to hsa-miR-3659). FIG. 13B shows an ROC curve for Example 6 (hsv1-miR-H18 to hsa-miR-3679-5p). In this case, because the diagnostic performance fell short of the standard, the sensitivity and specificity values are not shown in a separate manner.

FIG. 14A shows an ROC curve for Comparative Example 1 (hsa-miR-30a-5p to hsa-miR- 31-5p). FIG. 14B shows an ROC curve for Comparative Example 2 (hsa-miR-30c-5p to hsa-miR-31-5p). In this case, because the diagnostic performance fell short of the standard, the sensitivity and specificity values are not shown in a separate manner.

FIG. 16A shows an ROC curve for Example 1 (hsv2-miR-H9 to hsa-miR-3659). FIG. 16B shows an ROC curve for Example 2 (hsa-miR-1913 to hsa-miR-3659).

FIG. 17A shows an ROC curve for Example 3 (hsv2-miR-H9 to hsa-miR-3679-5p). FIG. 17B shows an ROC curve for Example 4 (hsa-miR-1913 to hsa-miR-3679-5p).

FIG. 18A shows an ROC curve for Example 5 (hsv1-miR-H18 to hsa-miR-3659). FIG. 18B shows an ROC curve for Example 6 (hsv1-miR-H18 to hsa-miR-3679-5p). In this case, because the diagnostic performance fell short of the standard, the sensitivity and specificity values are not shown in a separate manner.

FIG. 19A shows an ROC curve for Comparative Example 1 (hsa-miR-30a-5p to hsa-miR-31-5p). FIG. 19B shows an ROC curve for Comparative Example 2 (hsa-miR-30c-5p to hsa-miR-31-5p). In this case, because the diagnostic performance fell short of the standard, the sensitivity and specificity values are not shown in a separate manner.

DETAILED DESCRIPTION OF THE INVENTION

Figure 1:
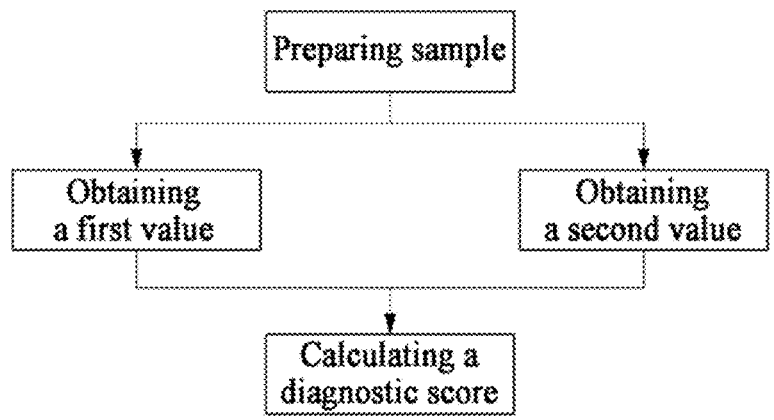
FIG. 1 shows a flowchart of a method of calculating a diagnostic score for prostate cancer. In this case, the processes of obtaining a first value and obtaining a second value represent processes that may be independently performed in parallel.
Figures 2A, 2B:
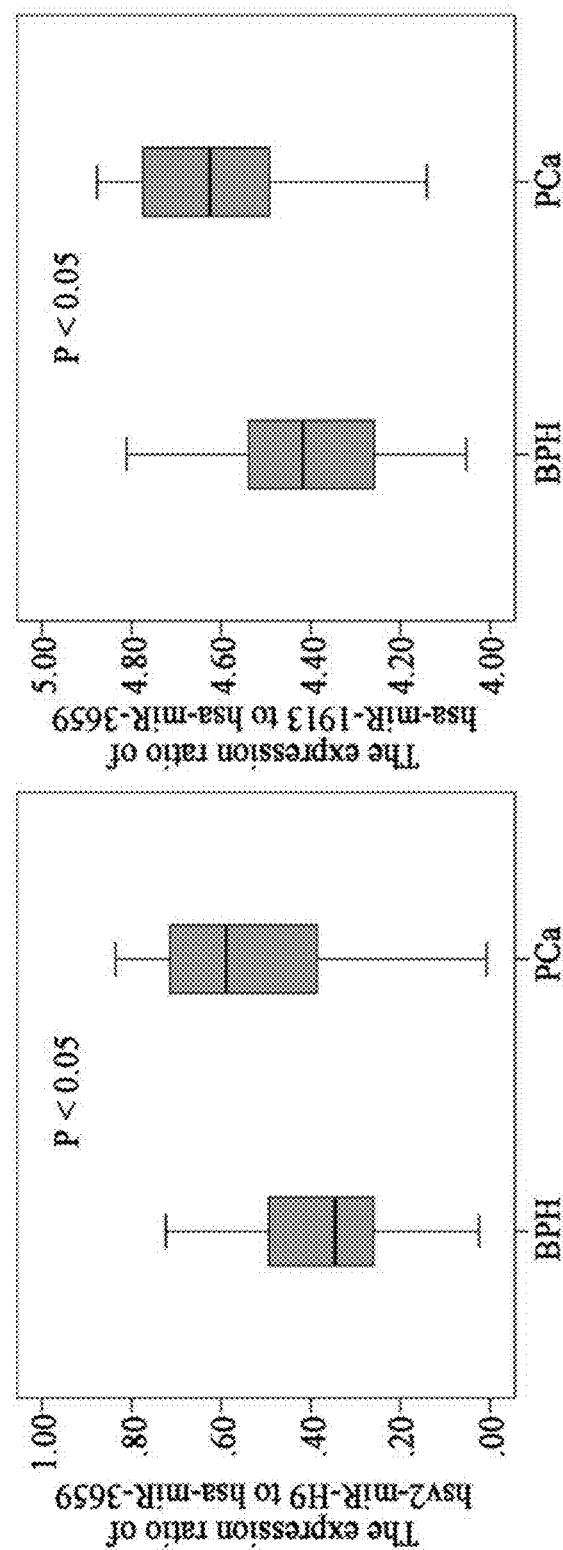
FIGS. 2A and 2B show graphs illustrating the statistical significance of difference in diagnostic scores between the group of benign prostatic hyperplasia subjects (BPH) and the group of prostate cancer subjects (PCa) as described in Examples 1 and 2 for all the experimental groups of subjects.
Figures 3A, 3B:
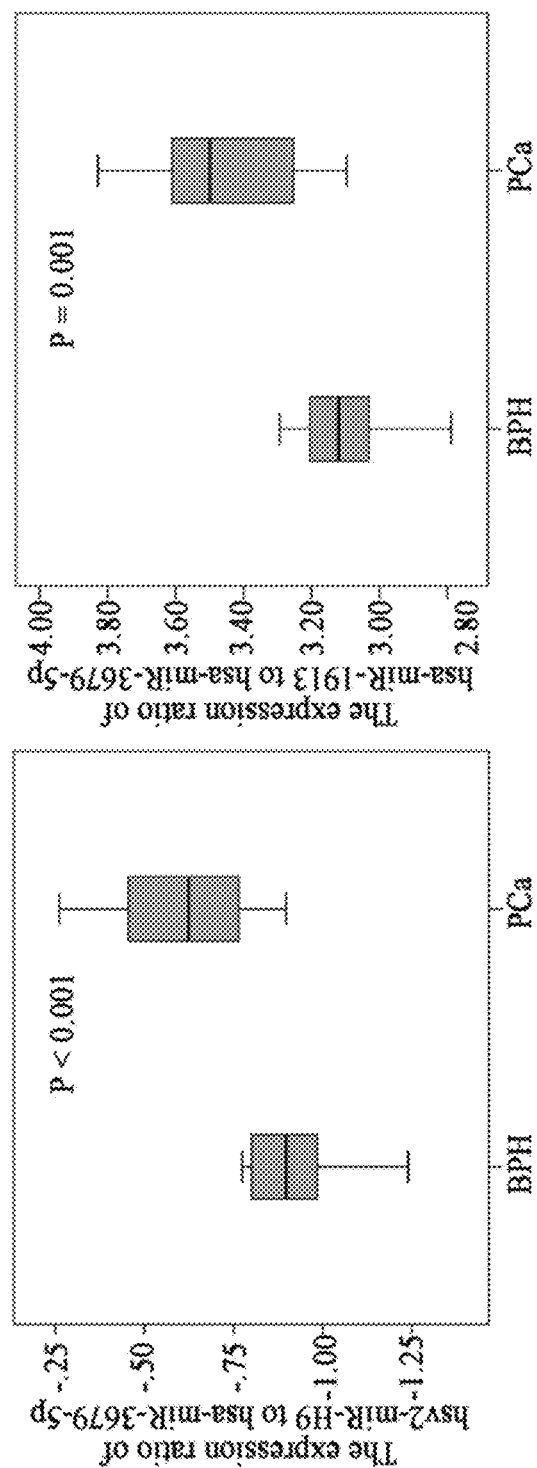
FIGS. 3A and 3B show graphs illustrating the statistical significance of difference in diagnostic scores between the group of benign prostatic hyperplasia subjects (BPH) and the group of prostate cancer subjects (PCa) as described in Examples 3 and 4 for all the experimental groups of subjects.

Hereinafter, the presently disclosed subject matter now will be described in more detail in terms of some specific embodiments and examples with reference to the accompanying drawings. It should be noted that the accompanying drawings encompass some, but not all embodiments of the present invention. The presently disclosed subject matter may be embodied in many different forms and should not be construed as limited to the specific embodiments set forth herein. Rather, these embodiments are provided so that this disclosure will satisfy applicable legal requirements. Indeed, many modifications and other embodiments of the present invention will come to the mind of one skilled in the art to which the presently disclosed subject matter pertains. Therefore, it is to be understood that the presently disclosed subject matter is not to be limited to the specific embodiments disclosed and that modifications and other embodiments are intended to be included within the scope of the appended claims.

Definitions of Terms

Approximately

The term "approximately" used in the present specification refers to an amount, level, value, number, frequency, percentage, dimension, quantity, weight, or length, which is changed to the degree of 30, 25, 20, 15, 10, 9, 8, 7, 6, 5, 4, 3, 2, or 1% with respect to a reference amount, level, value, number, frequency, percentage, dimension, size, weight, or length.

Subject

The term "subject" used in the present specification refers to an individual organism that is exposed to a certain material (for example, a peptide, and the like). The subject may mean an independent organism such as a human, an animal, and the like, and may also mean some components of the independent organism, such as a portion of a tissue, a cell, and the like. This meaning may be appropriately interpreted from context. Also, the term "subject" may encompass all the other meanings recognized by persons having ordinary skill in the art.

Diagnosis

The term "diagnosis" used in the present specification refers collectively to all types of direct and indirect actions that determine whether a subject is associated with a certain disease. In this case, the expression "associated with a certain disease" may include the onset of a relevant disorder, information on progression of the relevant disorder when the disorder develops, and the like. In the present specification, it should be understood that when the term "diagnose a certain disease" is used herein, the term encompasses confirmation of the onset of the certain disease as well as the probability, risk, and/or likelihood of developing the certain disease, and the like. This meaning may be appropriately interpreted from context. Also, the term "diagnosis" may encompass all the other meanings recognized by persons having ordinary skill in the art.

Biomarker

The term "biomarker" used in the present specification generally refers to an indicator that may sense a change in the subject's body, and includes a protein, DNA, RNA, and/or other metabolites. In a narrower sense, the term "biomarker" often refers to a target material (for example, a certain protein, or miRNA) that reflects information on whether a subject has a certain disease. This meaning may be appropriately interpreted in the context, and the term "biomarker" may encompass all the other meanings recognized by persons having ordinary skill in the art.

miRNA

The term "miRNA" or "micro RNA" used in the present specification refers to a small unexpressed RNA molecule consisting of 20 to 25 nucleotides, which has been found in plants, animals, viruses, and the like. miRNA is known to have functions such as control of gene expression, and the like. miRNA is found in cells as well as found in extracellular fluids. For a human, in particular, miRNA is particularly found in almost all body fluids in the body such as serum, plasma, as well as urine, saliva, tears, and the like. Therefore, the miRNA found in the extracellular fluids has been actively researched for use as a diagnostic biomarker for a certain disease (for example, cancer). The term "miRNA" or "micro RNA" may encompass all the other meanings recognized by persons having ordinary skill in the art.

Extracellular Vesicles

The term "extracellular vesicle" used in the present specification refers to a structure in a particulate form, which is surrounded by a lipid bilayer derived from cells and has no self-replicating function. The diameter of the extracellular varies widely from approximately 20 to 30 nanometers, and up to approximately 10 microns. The extracellular vesicles have various functions in a subject's body. In this case, extracellular vesicles have a representative function of enclosing proteins, lipids, and the like, which have various functions in the extracellular vesicles, and delivering them out of cells. The extracellular vesicles are referred to encompass all types of ectosomes, microvesicles, microparticles, exosomes, apoptotic bodies, large oncosomes, and exophers, but the present invention is not limited thereto. The term "extracellular vesicle" may encompass all the other meanings recognized by persons having ordinary skill in the art.

Background: Diagnosis of Prostate Cancer

Diagnosis of Prostate Cancer—Overview

In principle, a standard method of diagnosing prostate cancer is a biopsy in which a small amount of prostate tissue is collected from a subject, and then the development or presence of cancer cells is determined. However, the biopsy involves a very painful process for a subject. Therefore, it is undesirable to perform the biopsy only because the subject shows symptoms suspected of the onset of prostate cancer (for example, urinary symptoms such as polyuria, urodynia, and the like). Thus, when the subject shows symptoms suspected of the onset of prostate cancer, it is common to first determine whether a biopsy is required through a PSA test. A prostate-specific antigen (PSA) test is a diagnosis method which includes taking blood from a subject to measure a concentration of PSA in a blood sample and estimate the probability of the subject developing prostate cancer. Hereinafter, each of the diagnosis methods will be described in further detail.

PSA test

A PSA test is a kind of diagnosis method which includes taking blood from a subject suspected of having or at risk of developing of prostate cancer, measuring a concentration of a prostate-specific antigen (hereinafter referred to as "PSA") in blood, and predicting the probability of developing prostate cancer based on the concentration of PSA. The prostate-specific antigen is a protein primarily produced by cells in the prostate. The PSA is included in a small amount in blood of a normal subject having no prostate cancer, but the concentration of PSA generally tends to increase in blood of a prostate cancer patient. Therefore, the PSA concentration in blood may be used as an indicator for determining the onset of prostate cancer, but experts have a variety of opinions concerning the accuracy of the PSA concentration such as 1) the PSA concentration in blood generally tends to increase with age, and 2) the PSA concentration in blood does not increase according to the type of prostate cancer even when the subject develops cancer. Although there is somewhat of a difference in specific numerical values disclosed in documents, generally when the PSA concentration in blood is measured to be in a range of 3 ng/mL to 10 ng/mL, it is regarded as being in a gray zone in which it is difficult to confirm whether the subject falls within a high-risk group of subjects developing prostate cancer using the PSA test only.

Biopsy

In fact, it is necessary to diagnose the onset of prostate cancer through a biopsy in order to confirm whether a subject has developed prostate cancer. This is achieved through a method that includes taking a trace amount of prostate tissue from a subject to directly examine whether there are cancer cells in the prostate tissue. This has problems in that 1) a patient experiences pain because a biopsy needle is allowed to pass through the subject's anus to take a desired specimen, 2) there is a risk of misdiagnosis when a site in which cancer cells are present is not located accurately because it ends up taking a marginal specimen of a site through which a biopsy needle passes, and 3) wounds may occur in the subject's rectum, and the like during an examination process, resulting in infections, and the like. Therefore, there is a need for an auxiliary diagnosis method to increase the reliability of the biopsy and perform a biopsy restrictively for patients in actual need of examination. The PSA test has been used as one of these auxiliary diagnosis methods, but has many limitations in that its reliability is degraded, and it is impossible to exactly determine whether the prostate cancer develops when the test result is within a gray zone, and the like.

Background—Screening miRNA Biomarker

To use a certain miRNA as a biomarker for determining whether a subject has a certain disease, it first must be determined whether a certain miRNA is abnormally expressed in a subject having a certain disease, compared to a normal subject. A miRNA microarray is representative of the methods of screening the certain miRNA. A miRNA microarray analysis is a method of screening expression levels of most miRNAs, which are known to be expressed in humans, from the subject's body fluid sample. In this case, an expression level of miRNA in the subject's sample is mainly measured using a kit (for example, RNA 6000 Pico Chip Kit, Agilent Technologies, Santa Clara, Calif., USA) manufactured in advance in the art. Types of the miRNAs expressed in the humans include approximately 1,400 miRNAs (including approximately 1,200 miRNAs derived from humans, and approximately 150 miRNAs derived from viruses), the number of which is lower than the number of known human genes. Also, the sequences of the miRNAs are known in the art. Therefore, it is possible to screen almost all miRNAs in the subject. When a commercially available kit is used, it is possible to roughly obtain an expression level of miRNA in the subject's sample. Based on these results, when the expression levels of the miRNAs in the samples from a subject having a prostate cancer and a normal subject are compared, it is possible to find which miRNA is abnormally expressed in the subject having prostate cancer. However, because the kit may be used to obtain an approximate expression level only for a screening purpose and also has a normalization issue, an additional analysis is required to find a biomarker with accurate analysis ability. The miRNA microarray has an advantage in that it is possible to rapidly find a candidate group of biomarkers that may be used for diagnosis of prostate cancer, and thus has been widely used to screen for subjects of analysis prior to full-scale analysis work.

Limitations of the Prior Art

Advantages in Use of Urine Sample

When the infection of a certain disease, a degree of progression of a disease, and the like need to be diagnosed from the subject's body fluid sample, a urine sample from the subject has various advantages. First, because it does not require the use of an injection needle, unlike when the blood or tissue is used as the sample, it is easy to obtain a sample, and there is no fear of inflicting pain on a subject. In addition, when the certain disease is a male urinary disease, the urinary disease occurs in relatively close proximity to the urinary tract through the urine flows. Therefore, direct information on the male urinary disease is likely to be included in the urine sample, compared to the blood sample. Accordingly, it is desirable in many aspects to use the urine sample when a male urinary disease is diagnosed.

Advantages in Targeting Extracellular Vesicle-Derived Biomarker

Extracellular vesicles consist of a lipid bilayer and have a stable structure. Therefore, nucleic acids (for example, DNA, RNA, miRNA, or the like), protein fragments, or the like included in the extracellular vesicles may be retained in a stable state over time as long as the extracellular vesicles are not intentionally disrupted. This is contrary to the fact that the nucleic acids, protein fragments, or the like directly included in the body fluid sample (blood, urine, and the like) are easily decomposed over time by external factors. Therefore, when a material included in the extracellular vesicles is used as a biomarker target, there is an advantage in that the sample may be stored for an extended period of time. Because extracellular vesicles are also included in a urine sample, the extracellular vesicle-derived material may be used as a biomarker target in the urine sample after it is subjected to a proper pretreatment process.

Problem in Measuring Extracellular Vesicle-Derived Biomarker in Urine

When the extracellular vesicle-derived material in urine is used as the biomarker target, it has advantages in that 1) it is easy to secure a sample, 2) it is advantageous to diagnose a male urinary disease, and 3) it is easy to store the sample due to the aforementioned characteristics. However, the extracellular vesicle-derived material has distinct drawbacks that include 1) the absolute quantity of the extracellular vesicle-derived material (for example, miRNA, and the like) included in the urine is small, and 2) an amount of the biomarker target included in the urine varies widely depending on the condition of the sample or subject. To diagnose a certain disease based on the expression level of the biomarker target included in the sample, it is necessary to take a plurality of samples from a number of subjects to compare expression levels of the biomarker target in the respective samples. Therefore, the aforementioned drawbacks should be overcome to develop a diagnosis method using the extracellular vesicle-derived material in the urine as the biomarker target. To overcome the aforementioned drawbacks, a reliable normalization process for the expression level of the biomarker target in the sample is required.

Technical Solution and Limitations of the Prior Art

According to the prior art, as one of the normalization processes, there has been an attempt to find a housekeeping gene for an extracellular vesicle-derived biomarker (for example, miRNA) in urine, but the attempt has failed. Also, there has been an attempt to normalize using the total amount of miRNA in the sample (Yun et al., Int Neurourol J 2015; 19:17-84), and to bypass the necessity for normalization by calculating a ratio of the up-expressed biomarker and the down-expressed biomarker (U.S. Ser. No. 15/550, 416), but the effect is limited.

Method of Calculating Diagnostic Score for Prostate Cancer

Method of Calculating Diagnostic Score—Overview

The present specification provides a method of calculating a diagnostic score for prostate cancer using at least two values. The method of calculating a diagnostic score includes preparing a sample, measuring a first value, measuring a second value, and calculating a diagnostic score. In this case, a subject's urine sample is used as the sample. The first value is a value associated with a first target, hsa-miR-3659 or hsa-miR-3679 derived from extracellular vesicles. In this case, the miRNA includes information on the onset of prostate cancer. However, because the first value reflects an effect of an endogenous factor, it is necessary to normalize the first value for use in diagnosis of prostate cancer. The second value is a value associated with a second target, that is, an additional miRNA derived from extracellular vesicles in the sample. For example, the second target may be hsv2-miR-H9-5p or hsa-miR-1913 derived from extracellular vesicles, but the present invention is not limited thereto. The second value may be used as a normalization factor of the first value, and the second value also is informative of the onset of prostate cancer. The measuring of the first value and/or the measuring of the second value may include amplifying the first target and/or the second target by a polymerase chain reaction (PCR), and determining the results. A diagnostic score is calculated based on the first value and the second value obtained in the above process. In this case, the diagnostic score is capable of diagnosing the onset of prostate cancer in the subject.

First Characteristic of Method of Calculating Diagnostic Score—Using Urine Sample The method of calculating a diagnostic score provided in the present specification may be used to diagnose whether a subject has developed prostate cancer. The method of calculating a diagnostic score is characterized by using the urine sample to measure a biomarker included in the urine sample. This has advantages in that a method of taking a sample is convenient and economical, and there is no fear of inflicting pain on a subject. Also, because materials secreted from prostate cells may be directly included in the urine, the method of calculating a diagnostic score has an advantage in that it may be a more direct method, compared to a method of measuring a biomarker associated with prostate cancer from a blood sample.

Second Characteristic of Method of Calculating Diagnostic Score—Measuring Extracellular Vesicle-Derived miRNA The method of calculating a diagnostic score provided in the present specification is to calculate a diagnostic score for prostate cancer by measuring expression levels of at least two biomarkers in the sample. In this case, the biomarker is characterized in that it is miRNA included in extracellular vesicles in urine. Because the extracellular vesicles are surrounded by a lipid bilayer to have a stable structure, the materials (for example, miRNA) included in the extracellular vesicles are effectively protected from the effects of an external environment. Therefore, the extracellular vesicles have a characteristic of preserving the materials therein as long as the extracellular vesicles are not broken. Thus, when the miRNA included in the extracellular vesicles is used as a target to be measured, it has an advantage in that a sample may be stored for an extended period of time after the sample is taken from the subject. Also, it has an advantage in that the storage condition of the sample does not have a great effect on the calculation results of the diagnostic score.

Third Characteristic of Method of Calculating Diagnostic Score—Measuring Expression Level of hsa-miR-3659 or hsa-miR-3679

As disclosed in Korean Patent Application No. 10-2018-0045062, hsa-miR-3659 or hsa-miR-3679 may be used as a biomarker for prostate cancer. Because the method of calculating a diagnostic score provided in the present specification basically uses a value associated with the expression level of hsa-miR-3659 or hsa-miR-3679 in the subject, the diagnostic score calculated by the method is capable of diagnosing the onset of prostate cancer.

Fourth Characteristic of Method of Calculating Diagnostic Score—Using Normalization Factor Specialized for hsa-miR-3659 or hsa-miR-3679

The method of calculating a diagnostic score provided in the present specification is characterized by using a normalization factor specialized for the expression level of hsa-miR-3659 or hsa-miR-3679 included in the urine sample. In general, a biomarker for a housekeeping gene is found and used to normalize an expression level of the biomarker, but the method of calculating a diagnostic score provided in the present specification uses a normalization factor specialized for the targeted hsa-miR-3659 or hsa-miR-3679. When the biomarker for a housekeeping gene is used as the normalization factor, it has difficulties in that 1) it is generally a very difficult operation to find a biomarker for a housekeeping gene, and 2) no biomarker associated with a housekeeping gene has been clearly elucidated for miRNA derived from extracellular vesicles in urine. On the other hand, when a normalization factor specialized for the target is used, it has advantages in that 1) it is possible to avoid the difficulty of finding a biomarker for a housekeeping gene, and 2) it is possible to obtain more reliable results for the expression level of the target.

Fifth Characteristic of Method of Calculating Diagnostic Score—Using Prostate Cancer-Associated with Factor as Normalization Factor In the method of calculating a diagnostic score provided in the present specification, the normalization factor is also characterized by including information on whether the subject has developed prostate cancer. Therefore, one or more types of processed information may be deduced by combining information on prostate cancer which includes the expression level of the hsa-miR-3659 or hsa-miR-3679, and information on prostate cancer included in the normalization factor. For example, the processed information may be obtained by amplifying the information on the onset of prostate cancer.

Use of Diagnostic Score

The diagnostic score provided in the present specification may be 1) used to determine diagnostic criteria for the onset of prostate cancer, and 2) used for a method of diagnosing prostate cancer, which references the diagnostic criteria.

Preparation of Sample

Preparation of Sample—Overview

The preparation of a sample from a subject included in the method of calculating a diagnostic score provided in the present specification includes preparing a urine sample from a subject. The preparation of the urine sample may further include performing proper pretreatment to measure an amount of miRNA derived from the extracellular vesicles included in the urine sample. According to one embodiment, the preparation of the sample may include disrupting extracellular vesicles included in the urine sample.

Type of Sample

The sample is a urine sample from a subject. According to one embodiment, the urine sample may be a urine sample collected first in in the morning from the subject. According to one embodiment, the urine sample may be a supernatant sample of urine collected from the subject. According to one embodiment, the urine sample may be a supernatant sample of the product obtained after the subject's urine is centrifuged.

Sample Volume

A volume of the urine sample is not particularly limited and may be properly selected according to need.

Sample Storage Temperature

A storage temperature for urine samples is not particularly limited as long as it is a temperature at which a target biomarker included in the sample may be safely stored.

Sample Including Extracellular Vesicles

The urine sample includes extracellular vesicles secreted from the subject's cells. According to one embodiment, the extracellular vesicles may be exosomes. According to one embodiment, the extracellular vesicles may include one or more selected from the group consisting of exosomes, microvesicles, and apoptotic bodies.

Subdivision of Sample

The urine sample may be used after it is subdivided when necessary. According to one embodiment, a first sample may be divided into a first subsample and a second subsample. According to one embodiment, a second sample may be divided into three or more subsamples.

Preparation of Sample—Example

The preparation of the urine sample is not particularly limited as long as it is a process required to obtain the first value and the second value. According to one embodiment, the preparation of the sample may include preparing a urine supernatant sample from a subject. The preparation of the sample may further include pretreating the sample. The pretreatment of the sample is not particularly limited as long as it is a process required to measure a value corresponding to an expression level of the desired extracellular vesicle-derived miRNA. According to one embodiment, the preparation of the urine sample may further include extracting miRNA in the urine using a kit suitable for the subject's urine sample. In some embodiments, a known kit may be used, and may be, for example, a Genolution urine miRNA purification kit (Genolution Pharmaceuticals Inc., Seoul, Korea), but the present invention is not limited thereto.

Obtaining First Value

Obtaining First Value—Overview

In the method of calculating a diagnostic score provided in the present specification, the first value is a value associated with the extracellular vesicle-derived hsa-miR-3659 or hsa-miR-3679 capable of diagnosing prostate cancer. According to one embodiment, the first value may be a value corresponding to an amount of the first target included in the sample. In this case, the first target is hsa-miR-3659 and/or hsa-miR-3679 derived from extracellular vesicles. The first value is informative of whether the subject has prostate cancer. However, it is difficult to use the first value alone to determine whether a subject has prostate cancer because an effect of various endogenous factors is also reflected in the first value along with the information on whether the subject has prostate cancer. According to one embodiment, the first value may reflect a first information capable of diagnosing prostate cancer, and a first noise caused by an endogenous factor independent of the first information at the same time. The method of obtaining a first value is not particularly limited as long as it is a method capable of calculating a value corresponding to an amount of the extracellular vesicle-derived hsa-miR-3659 or hsa-miR-3679. According to one embodiment, obtaining of the first value may include amplifying one or more miRNAs in the sample using a polymerase chain reaction (PCR), and calculating an amount of the one or more miRNAs in the sample from the results of amplification.

Targeting Extracellular Vesicle-Derived hsa-miR-3659 or hsa-miR-3679 in Urine

The first value is a value associated with the extracellular vesicle-derived hsa-miR-3659 or hsa-miR-3679 capable of diagnosing prostate cancer. This corresponds to a biomarker including information on the onset of prostate cancer, which has been found using a miRNA assay method. The present inventors have conducted research and found that the extracellular vesicle-derived hsa-miR-3659 and hsa-miR-3679 in a subject's urine is down-expressed in subjects having prostate cancer, compared to the normal subjects. Therefore, the method of determining a diagnostic score provided in the present specification includes measureing the amount of the target included in the sample using, as the target, extracellular vesicle-derived hsa-miR-3659 and/or hsa-miR-3679 included in a subject's urine sample.

Example of Method of Obtaining First Value—PCR

According to one embodiment, obtaining of the first value may include amplifying the extracellular vesicle-derived hsa-miR-3659 or hsa-miR-3679 in a urine sample by a polymerase chain reaction (PCR), and obtaining a first value from the results of amplification. In this case, the method of amplification using PCR may be properly selected from the methods known to persons having ordinary skill in the art. According to one embodiment, obtaining of the first value may further include synthesizing cDNA of a first target using the extracellular vesicle-derived hsa-miR-3659 and/or hsa-miR-3679 in the sample as the first target; mixing the cDNA with a reaction reagent, which includes one or more primers selected from the group consisting of SEQ ID NOs: 1 and 2, to prepare a mixture for PCR amplification; amplifying the mixture for PCR amplification by RT-PCR; and calculating an amount of the first target included in the sample from the RT-PCR results. According to one embodiment, the RT-PCR results may include a reaction cycle number vs. fluorescence signal intensity graph and/or a melting curve. According to one embodiment, the obtaining of the first value may be performed using a known PCR apparatus. Specifically, the PCR apparatus may be Rotor Gene 6000 instrument (Qiagen, Hilden, Germany), but the present invention is not limited thereto.

Limitations of Use of First Value Alone—Effect of Endogenous Factor

Even when an amount of the extracellular vesicle-derived hsa-miR-3659 or hsa-miR-3679 included in the subject's sample is informative of whether the subject has developed prostate cancer, the first value may not be used alone to diagnose the onset of prostate cancer and/or a degree of progression of prostate cancer. This is because the information on the onset of prostate cancer and an effect of an endogenous factor independent of the information are simultaneously reflected in the first value. Therefore, unless the effect of the endogenous factor is removed, reduced, and/or controlled, it is difficult to use the first value alone to diagnose the onset of prostate cancer and/or the degree of progression of prostate cancer. The endogenous factor refers to various factors independent of prostate cancer, and will be described in further detail, as follows.

Endogenous Factor

Endogenous Factor—Definition

When an expression level of a biomarker for a certain disease is measured, there are various factors that have an influence on the expression level of the biomarker. In the present specification, refers collectively to factors associated with the sample or subject itself among the factors that affect the expression level of the biomarker, rather than the factors associated with the certain disease (for example, the onset and progression of the certain disease). Because the amount of the biomarker included in the sample not only reflects an effect of the certain disease but also an effect of the endogenous factor, it is very important to remove, reduce and/or control the effect of the endogenous factor in order to use the expression level of the biomarker to diagnose a certain disease.

First Example of Endogenous Factor—Sample-Related Factor

The endogenous factor may include a sample-related factor. The expression "sample-related factor" refers collectively to factors associated with the attributes of the sample itself among the factors that may affect the expression level of the biomarker in the sample. According to one embodiment, the endogenous factor may include one or more sample-related factors. Specifically, the sample-related factors may include a volume of the sample, a sample collection time, a method of collecting a sample, a sample storage duration, a sample storage temperature, or a method of subdividing a sample, but the present invention is not limited thereto.

Second Example of Endogenous Factor—Subject-Related Factor

The endogenous factor may include a subject-related factor. The expression "sample-related factor" refers collectively to factors associated with the physiological activities, conditions, and the like, which are independent of the onset of prostate cancer, in the subject, among the factors that may affect the expression level of the biomarker in the sample. According to one embodiment, the endogenous factor may include one or more subject-related factors. Specifically, the sample-related factors may include a gender of the subject, an age of the subject, a race of the subject, a weight of the subject, a renal function of the subject, or a hydration state of the subject before collection of the sample, but the present invention is not limited thereto.

Obtaining Second Value

Obtaining Second Value—Overview

The second value is associated with extracellular vesicle-derived miRNA in the sample. According to one embodiment, the second value may correspond to an amount of the extracellular vesicle-derived miRNA included in the sample. Specifically, the extracellular vesicle-derived miRNA may be hsv2-miR-H9-5p or hsa-miR-1913, but the present invention is not limited thereto. Also, the second value is informative of whether the subject has developed prostate cancer. In addition, the effect of the endogenous factor is reflected in the second value. In this case, the effect of the endogenous factor reflected in the second value has a close correlation with an extent of the effect of the endogenous factor reflected in the first value. Therefore, the first value may be normalized using the second value. In other words, the effect of the endogenous factor reflected in the first value may be removed, reduced, and/or controlled using the second value. According to one embodiment, the second value may be informative of whether the subject has developed prostate cancer and third information associated with the endogenous factor. In this case, the third information has a close correlation with the first noise, and thus the first value may be normalized using the second value.

Targeting Extracellular Vesicle-Derived miRNA

The second value is associated with the extracellular vesicle-derived miRNA in the sample. To remove the effect of the endogenous factor reflected in the first value, a value that is independent of the first value and reflects the same effect of the endogenous factor is required. A value associated with the expression level of the extracellular vesicle-derived miRNA is preferably used as the second value because it is thought to have the same or similar effect of the endogenous factor since the first value is also a value associated with the expression level of extracellular vesicle-derived miRNA (hsa-miR-3659 or hsa-miR-3679). According to one embodiment, the second value may be a value corresponding to an amount of extracellular vesicle-derived miRNA included in the sample.

First Characteristic of Second Value—Including Information on Endogenous Factor

Like the first value, the second value reflects the effect of the endogenous factor. As described above, the endogenous factor includes one or more sample-related factors and/or one or more subject-related factors.

Second Characteristic of Second Value—Including Information Associated with Prostate Cancer Like the first value, the second value also is informative of whether the subject has developed prostate cancer. However, the information on the onset of prostate cancer included in the second value is independent of the information included in the first value. According to one embodiment, the second value may correspond to an amount of the second target included in the sample. In this case, the second value may be informative of whether the subject has developed prostate cancer. According to one embodiment, the second target may be up-regulated in subjects who have developed prostate cancer, compared to normal subjects or subjects with benign prostatic hyperplasia. According to still another embodiment, the second target may be down-regulated in subjects who have developed prostate cancer, compared to the normal subjects or subjects with benign prostatic hyperplasia. According to one embodiment, the second target may be hsv2-miR-H9-5p, hsv1-miR-H18, or hsa-miR-1913 derived from extracellular vesicles.

Third Characteristic of Second Value—Close Correlation with Effect of Endogenous Factor Reflected in First Value As such, the second value is characterized by 1) targeting extracellular vesicle-derived miRNA, 2) including information associated with prostate cancer, and 3) including the information on the endogenous factor. However, even when the second value satisfies these three conditions, it may not be utilized as the second value in the method of calculating a diagnostic score provided in the present specification. This is because the purpose of obtaining the second value is to remove, reduce, and/or control the effect of the endogenous factor reflected in the first value. Therefore, the effect of the endogenous factor reflected in the second value has to have a close correlation with the effect of the endogenous factor reflected in the first value. When the second value provided in the present specification is used, the effect of the endogenous factor reflected in the first value may be removed, reduced, and/or controlled. According to one embodiment, the second value may include third information that has a close correlation with the first noise that is the effect of the endogenous factor reflected in the first value.

Example of Method of Obtaining Second Value—PCR

According to one embodiment, obtaining of the second value may include amplifying the extracellular vesicle-derived miRNA in the urine sample by PCR, and obtaining a second value from the results of amplification. A specific PCR method is as described in the section "Example of method of obtaining first value—PCR". In this case, a specific sequence of a primer included in a reaction reagent mixed with the cDNA may vary depending on the sequence of the extracellular vesicle-derived miRNA as the target for calculating a second value. According to one embodiment, when obtaining of the second value is performed using extracellular vesicle-derived hsv2-miR-H9-5p and/or hsa-miR-1913 as the second target, the primer included in the reaction reagent may have one or more sequences selected from the group consisting of SEQ ID NOs: 3 to 4.

Relationship Between Processes of Obtaining of First Value and Obtaining of Second Value When the obtaining of the first value and the obtaining of the second value, which are included in the method of calculating a diagnostic score for prostate cancer provided in the present specification, satisfy the aforementioned conditions and characteristics, each order and method are not particularly limited. According to one embodiment, the obtaining of the first value and the obtaining of the second value may be performed at the same time. According to another embodiment, the obtaining of the first value and the obtaining of the second value may be performed in a sequential manner. For example, the second value may be obtained after the first value is obtained. By way of another example, the first value may be obtained after the second value is obtained. According to one embodiment, the obtaining of the first value and the obtaining of the second value may be performed by the same method. Specifically, the obtaining of the first value and the obtaining of the second value may be performed by means of the same PCR method. In addition, the obtaining of the first value and the obtaining of the second value may be performed using the same PCR apparatus. According to still another embodiment, the obtaining of the first value and the obtaining of the second value may be performed by different methods. According to one embodiment, the obtaining of the first value and the obtaining of the second value may be performed in the sample without other separation processes. According to another embodiment, after the sample is subdivided into two or more subsamples, the obtaining of the first value and the obtaining of the second value may be separately performed on the subsamples. Specifically, the sample may be subdivided into a first subsample and a second subsample, the first value may be obtained from the first subsample, and the second value may be then obtained from the second subsample.

Calculating Diagnostic Score

Calculating Diagnostic Score—Overview

The method of calculating a diagnostic score provided in the present specification may include calculating the diagnostic score using the first value and the second value obtained from the obtaining of the first value and the obtaining of the second value as described above. According to one embodiment, the calculating of the diagnostic score for prostate cancer is performed using the first value and the second value. As a result, the diagnostic score may be used to diagnose prostate cancer.

Characteristics of Diagnostic Score—Reflecting Information on Prostate Cancer-Related Biomarker Because the diagnostic score is obtained by normalizing the effect of the endogenous factor reflected in the first value using the second value, the diagnostic score includes information associated with the onset of prostate cancer and/or the degree of progression of prostate cancer reflected in the first value. Therefore, the diagnostic score is capable of diagnosing prostate cancer.

Examples of Method of Calculating Diagnostic Score

The calculation of the diagnostic score is not particularly limited as long as it satisfies the following two conditions: 1) using both the first value and the second value, and 2) removing, reducing, and/or controlling the effect of the endogenous factor reflected in the first value and the second value in the diagnostic score. According to one embodiment, the diagnostic score may be calculated by a ratio of the first value and the second value.

Method of Determining Test Criteria for Diagnosis of Prostate Cancer

Method of Determining Test Criteria for Diagnosis of Prostate Cancer—Overview

The present specification provides a method of determining test criteria for diagnosis of prostate cancer using the diagnostic score for prostate cancer. Because the diagnostic score for prostate cancer has different patterns (for example, different average values of the diagnostic scores for individual groups of subjects) for the group of subjects who have developed prostate cancer and the group of subjects who have not developed prostate cancer, the prostate cancer test diagnostic criteria may be determined when a distribution of the diagnostic scores for individual subjects is analyzed for a cohort in which the onset of prostate cancer in the individual subjects is known in advance. According to one embodiment, the method of determining test criteria for diagnosis of prostate cancer includes obtaining a data set, which includes information on the onset of prostate cancer and a diagnostic score for prostate cancer, from the subjects included in the cohort; and determining test criteria for diagnosis of prostate cancer from the data set. In this case, the cohort includes one or more subjects who have developed prostate cancer, and one or more subjects who have not developed prostate cancer. Also, the diagnostic score for prostate cancer is calculated by the method of calculating a diagnostic score for prostate cancer provided in the present specification.

Cohort

The method of determining test criteria for diagnosis of prostate cancer requires the information on the onset of prostate cancer in one or more subjects and the diagnostic scores for prostate cancer. Therefore, the method targets a cohort including one or more subjects who have not developed prostate cancer, and one or more subjects who have developed prostate cancer. According to one embodiment, the method of determining test criteria for diagnosis of prostate cancer may be performed on the cohort including one or more subjects who are normal or have developed benign prostatic hyperplasia, and subjects who have developed prostate cancer.

Obtaining Data Set

The method of determining test criteria for diagnosis of prostate cancer includes obtaining a data set, which includes the information on the onset of prostate cancer and the diagnostic score for prostate cancer, from each of the subjects included in the cohort. According to one embodiment, the method of determining test criteria for diagnosis of prostate cancer includes calculating a first data set, wherein the first data set includes a list of information on whether each subject in a cohort has developed prostate cancer, and a list of diagnostic scores for the individual subjects in the cohort. In this case, the diagnostic scores are calculated by the method of calculating a diagnostic score for prostate cancer provided in the present specification.

Determining Test Criteria for Diagnosis of Prostate Cancer

The method of determining test criteria for diagnosis of prostate cancer includes determining test criteria for diagnosis of prostate cancer from the data set. The test criteria for diagnosis of prostate cancer provide a standard for determining whether the subject has developed prostate cancer when the diagnostic score is obtained from a subject whose development of prostate cancer is unknown. According to one embodiment, the determining of the test criteria for diagnosis of prostate cancer from the data set may be performed in consideration of the sensitivity and specificity of the test criteria. For example, the test criteria may provide a standard for maximizing sensitivity and the specificity. By way of another example, the test criteria may provide a standard for representing a value greater than or equal to a certain sensitivity value. By way of still another example, the test criteria may provide a standard for representing a value greater than or equal to a certain specificity value. According to one embodiment, the test criteria for diagnosis of prostate cancer may provide a probability of developing prostate cancer depending on the diagnostic score value.

Method of Providing Information on Diagnosis of Prostate Cancer

The present specification discloses a method of providing information on diagnosis of prostate cancer using the diagnostic score. In this case, the test criteria for diagnosis of prostate cancer may be used. According to one embodiment, the method of providing information on diagnosis of prostate cancer may include calculating the diagnostic score for prostate cancer in a subject; and determining a risk factor for prostate cancer from the diagnostic score with reference to one or more predetermined values. In this case, the one or more predetermined values may be the test criteria for diagnosis of prostate cancer.

Method of Calculating Diagnostic Score for Prostate Cancer—Summary

The present specification provides a method of calculating a diagnostic score for prostate cancer by combining at least two values. The method of calculating a diagnostic score for prostate cancer includes preparing a sample, obtaining a first value, obtaining a second value, and calculating a diagnostic score. The sample is characterized in that it is a subject's urine sample, the first value is a value that corresponds to an amount of a first target included in the sample, wherein hsa-miR-3659 or hsa-miR-3679-5p derived from extracellular vesicles included in the sample is used as the first target, and the second value is a value that corresponds to an amount of a second target included in the sample, wherein miRNA derived from extracellular vesicles included in the sample is used as the second target. Both the first value and the second value include information on whether the subject has developed prostate cancer, and the second value corresponds to a normalization factor specialized for the first value. Therefore, the diagnostic score for prostate cancer calculated according to the method is characterized by being capable of diagnosing prostate cancer. The present specification provides a use of the diagnostic score for prostate cancer. 1) The diagnostic criteria for prostate cancer may be determined using the diagnostic score for prostate cancer, and 2) the information on diagnosis of the onset of prostate cancer using the diagnostic score for prostate cancer and the diagnostic criteria for prostate cancer may be provided.

EXPERIMENTAL EXAMPLES

Hereinafter, the present invention provided in the present specification will be described in further detail with reference to Experimental Examples and Examples thereof. However, it will be apparent to those skilled in the art that these Examples are provided only for illustrating the present invention, and are not intended to be construed as limiting the scope of the disclosure set forth in the present specification.

Experimental Example 1: Test Subjects and Sample Preparation

Experimental Example 1.1: Test Subjects

To calculate a diagnostic score for prostate cancer, an experimental group of subjects from which samples were to be taken was prepared. The experimental group of subjects included both patients with benign prostatic hyperplasia (BPH), which did not develop prostate cancer, and patients who had developed prostate cancer. The characteristics of the experimental group of subjects are as listed in Table 1 below.

TABLE 1

| Information on test subjects | | | |
|---|---|---|---|
| Variables | BPH | Pca | p-value |
| Number of patients | 14 | 12 | |
| Number of patients (PSA 3 to 10 ng/mL) | 6 | 5 | |
| Age (mean ± SD) | 74.21 ± 7.50 | 68.83 ± 5.87 | 0.080 |
| PSA ± SD (ng/mL) | 3.28 ± 3.88 | 6.92 ± 181.30 | 0.035 |
| Operation (%) | | | <0.001 |
| TURP | 14 (100.00) | 2 (16.67) | |
| Radical prostatectomy | | 10 (83.33) | |
| Gleason score (%) | | | |
| 7 (3 + 4) | | 7 (58.33) | |
| 7 (4 + 3) | | 3 (25.00) | |
| 8≥ | | 2 (16.67) | |
| TNM stage (%) | | | |
| T2 | | 6 (50.00) | |
| T3 | | 4 (33.33) | |
| T4 or metastasis | | 2 (16.67) | |

BPH: benign prostatic hyperplasia; PCa: prostate cancer; SD: standard deviation; PSA: prostate-specific antigen; TURP: transurethral resection of the prostate. P-values are values calculated by a Mann-Whitney U-test using urine samples from subjects with BPH and PCa.

Experimental Example 1.2: Sample Preparation

Samples from each group of subjects prepared in Experimental Example 1.1 were prepared. The sample preparation was as follows.
(1) A subject's urine was collected in the morning.
(2) The urine sample was centrifuged at 2,500 rpm for 15 minutes using a centrifuge.
(3) The urine supernatant was collected as the sample, and stored at −20° C. until use in the next process.

Experimental Example 1.3: Sample Pretreatment

The urine sample prepared in Experimental Example 1.2 was subjected to a pretreatment process for calculating a first value and a second value. This process is as follows.
(1) A Genolution urine miRNA purification kit (Genolution Pharmaceuticals Inc., Seoul, Korea) was used to purify the urine sample.
(2) 500 μL of the urine sample supernatant was added into a tube containing a Genolution proprietary miRNA separation solution, and vortexed for 20 seconds.
(3) 200 μL of chloroform was added into the tube, and vortexed for 10 seconds.

(4) After the step (3), the tube was centrifuged at 4° C. and 13,000 rpm for 10 minutes.
(5) After the step (4), 650 μL of a liquid phase was removed from the top of the tube. In this case, care was taken not to remove a white precipitate in the tube.
(6) The sample remaining in the tube after the step (5) was transferred to a new 1.5 mL tube, and 0.8 mL of isopropanol was added thereto.
(7) After the step (6), the tube was centrifuged at 4° C. and 15,000 rpm for 20 minutes.
(8) After the step (7), the tube was tilted in an opposite direction of an RNA pellet to pour out a liquid phase.
(9) After the step (8), 500 μL of 70% EtOH was added to the tube.
(10) After the step (9), the tube was centrifuged at 4° C. and 15,000 rpm for 20 minutes.
(11) After the step (10), the residual ethanol was removed from the tube, and the remaining pellet was then dissolved in 40 μL of RNase-free water, and stored at −80° C. until use.

Experimental Example 2: Measurement of Amount of Target miRNA Included in Sample An amount of the target miRNA included in the sample prepared in Experimental Example 1 was calculated by a PCR method. A specific PCR method is as follows.
(1) cDNA was synthesized from the sample prepared in Experimental Example 1.3 using a Mir-X™ miRNA First Strand cDNA Synthesis kit (TAKARA BIO, Otsu, Japan). In this case, the cDNA synthesis method was performed according to the manufacturer's protocol.
(2) The product of the step (1) was added into a micro-reaction tube (Corbett Research, Mortlake, Australia) containing SYBR Premix EX Taq (TAKARA BIO) in a final volume of 10 μL, and subjected to RT-PCR analysis using Rotor-Gene Q instrument (Qiagen, Valencia, Calif., USA). In this case, the primers (RNA oligonucleotides) (Integrated DNA Technologies (IDT), Seoul, Korea) corresponding respectively to the target miRNAs were used to plot standard curves of the target miRNAs. The sequences of the target miRNAs and the primers used are as listed in Table 2 below.

TABLE 2

List of target miRNAs and corresponding primer sequences

| Target miRNA | Primer sequence (RNA oligonucleotides | SEQ ID NO |
| --- | --- | --- |
| hsa-miR-3659 | 5'-TGA GTG TTG TCT ACG AGG GCA-3' | 1 |
| hsa-miR-3679-5p | 5'-TGA GGA TAT GGC AGG GAA GGG GA-3' | 2 |
| hsv2-miR-H9 | 5'-CTC GGA GGT GGA GTC GCG GT-3' | 3 |
| hsv1-miR-H18 | 5'-CCC GCC CGC CGG ACG CCG GGA CC-3' | 4 |
| hsa-miR-1913 | 5'-TCT GCC CCC TCC GCT GCC A-3' | 5 |
| hsa-miR-30a-5p | 5'-TGT AAA CAT CCT CGA CTG GAA G-3' | 6 |
| hsa-miR-30c-5p | 5'-TGT AAA CAT CCT ACA CTC TCA GC-3' | 7 |
| hsa-miR-31-5p | 5'-AGG CAA GAT GCT GGC ATA GCT-3' | 8 |

(3) The standard curve was plotted in a range of 2.25×105 to 2.25×108, and all the samples were measured in triplicate. In this case, the RT-PCR conditions were set according to the manufacturer's protocol.
(4) Rotor-Gene Q software 2.3.1.49 was used to collect and analyze the spectrum data as the output.

Experimental Example 3: Statistical Analysis

Experimental Example 3.1: Calculation of Diagnostic Score

The diagnostic score was calculated using the amount of the target miRNA included in the sample obtained in Experimental Example 2 as the first value or the second value. The diagnostic score was calculated by a ratio of the amounts of the two target miRNAs included in the sample. Specific targets used in Examples are listed in Table 3 below.

TABLE 3

| Number | First target | Second target |
| --- | --- | --- |
| Example 1 | hsa-miR-3659 | hsv2-miR-H9 |
| Example 2 | hsa-miR-3659 | hsa-miR-1913 |
| Example 3 | hsa-miR-3679-5p | hsv2-miR-H9 |
| Example 4 | hsa-miR-3679-5p | hsa-miR-1913 |
| Example 5 | hsa-miR-3659 | hsv1-miR-H18 |
| Example 6 | hsa-miR-3679-5p | hsv1-miR-H18 |
| Comparative Example 1 | hsa-miR-31-5p | hsa-miR-30a-5p |
| Comparative Example 2 | hsa-miR-31-5p | hsa-miR-30c-5p |

Experimental Example 3.2: Verification of Analysis Ability in Each Example

To verify an ability to diagnose prostate cancer using the diagnostic scores of the respective Examples calculated in Experimental Example 3.1, statistical analysis was performed as follows.
(1) The diagnostic scores of the respective Examples were calculated using a Mann-Whitney U-test to determine whether there was a statistically significant difference in the diagnostic scores between the groups of subjects. The statistical significance was calculated for i) all subjects who had developed prostate cancer with respect to all BPH subjects, and ii) the group of prostate cancer subjects in a PSA gray zone with respect to the group of BPH subjects in a PSA gray zone (PSA concentration: 3 ng/L to 10 ng/L).
(2) To set up the optimal cutoff standard capable of deducing the highest specificity and sensitivity, receiver operating characteristic (ROC) curves were derived for the experimental groups of subjects in each Example. Also, the area under the curve (AUC) and the optimal sensitivity and specificity were derived for the ROC curves. The ROC curves were derived for i) all the groups of subjects, and ii) the groups of subjects in the PSA gray zone, respectively.

Experimental Example 4. Results

Figures 4A, 4B:
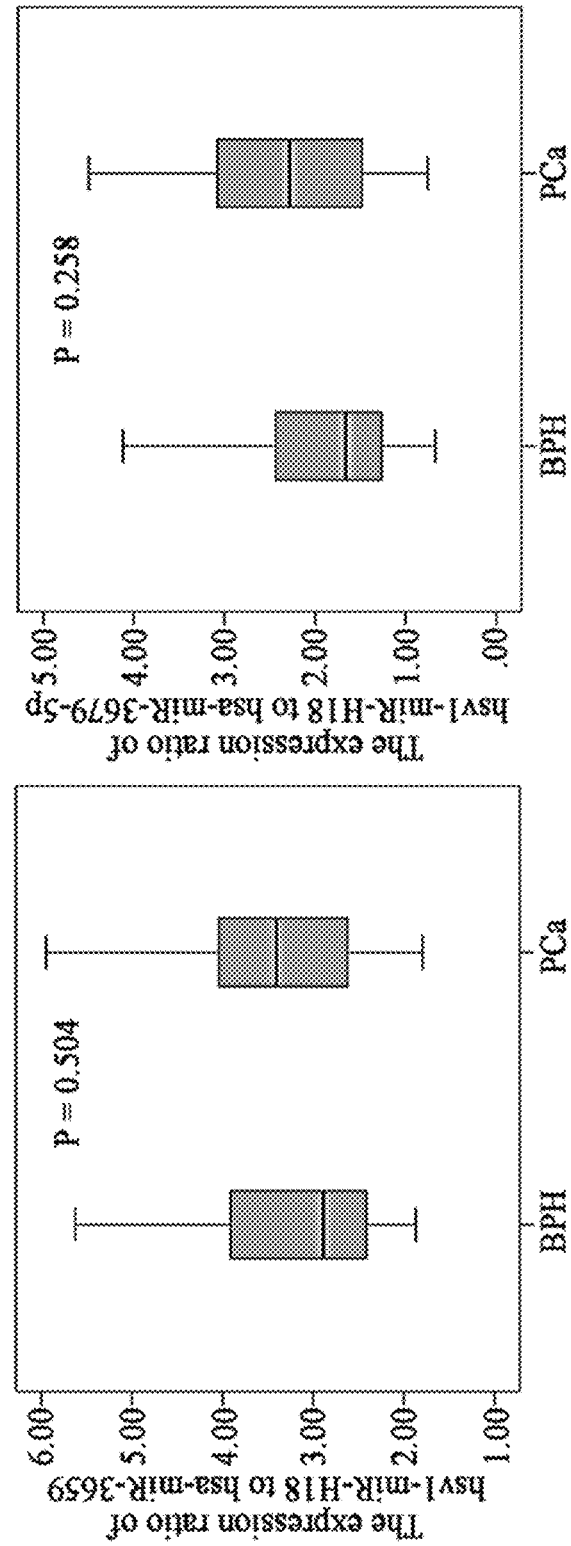
FIGS. 4A and 4B show graphs illustrating the statistical significance of difference in diagnostic scores between the group of benign prostatic hyperplasia subjects (BPH) and the group of prostate cancer subjects (PCa) as described in Examples 5 and 6 for all the experimental groups of subjects.
Figures 5A, 5B:
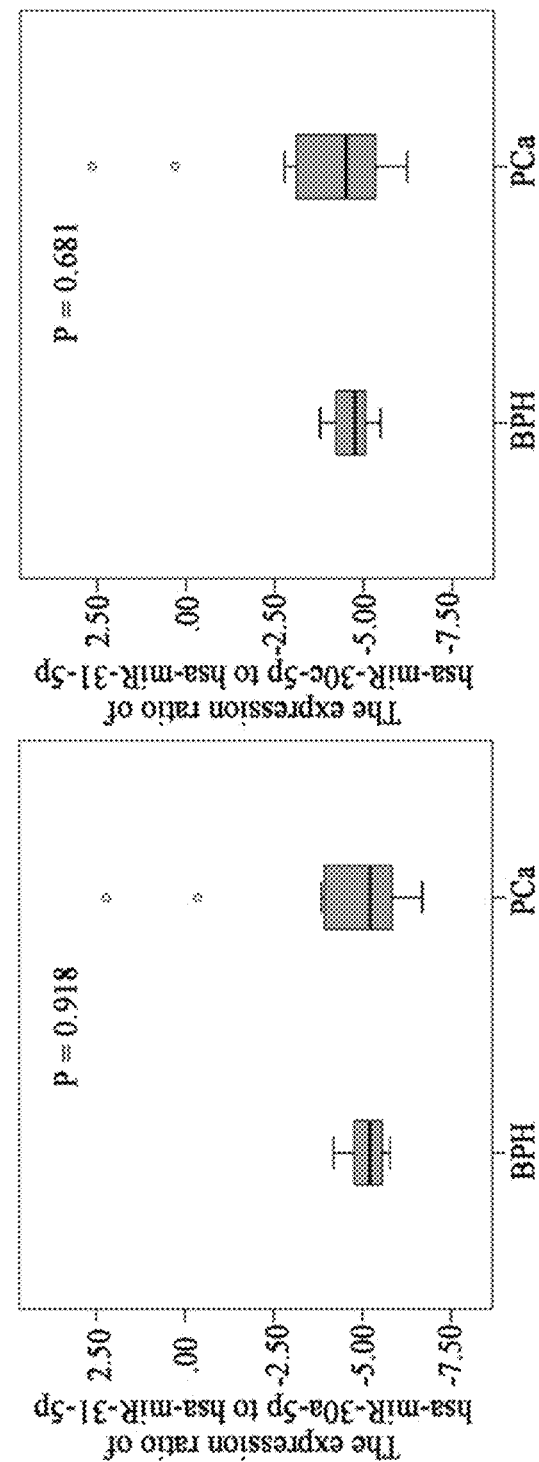
FIGS. 5A and 5B show graphs illustrating the statistical significance of difference in diagnostic scores between the group of benign prostatic hyperplasia subjects (BPH) and the group of prostate cancer subjects (PCa) as described in Comparative Examples 1 and 2 for all the experimental groups of subjects.
Figures 6A, 6B:
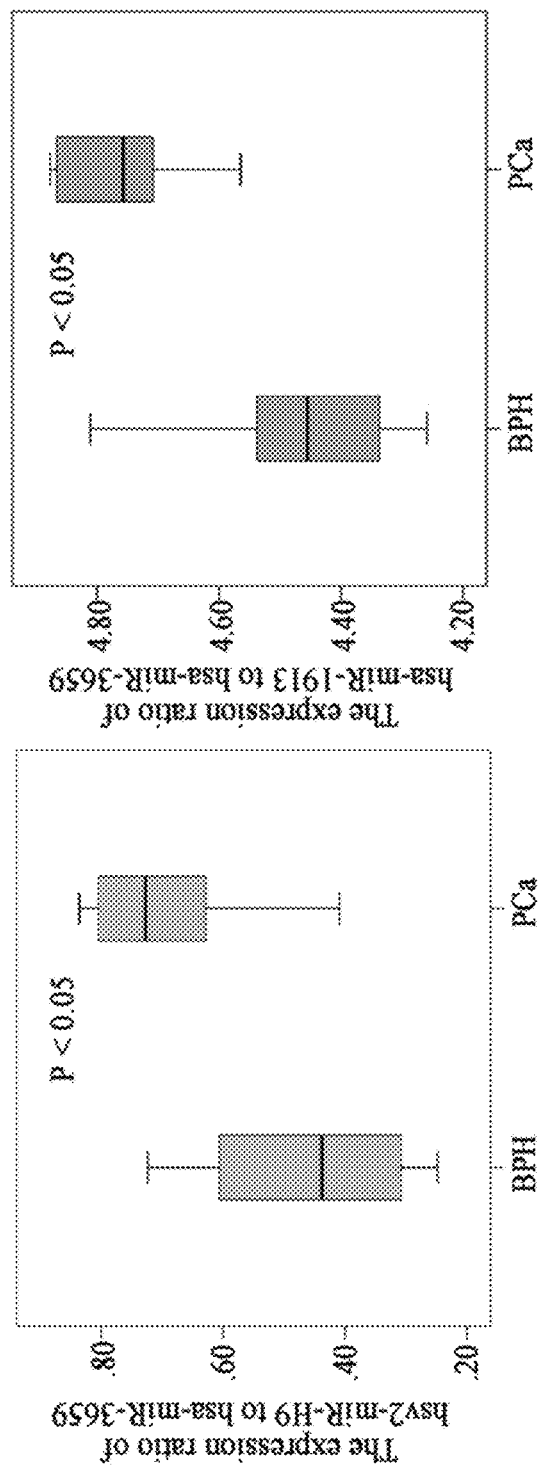
FIGS. 6A and 6B show graphs illustrating the statistical significance of difference in diagnostic scores between a group of benign prostatic hyperplasia subjects (BPH) and a group of prostate cancer subjects (PCa) as described in Examples 1 and 2 for groups of subjects in a PSA gray zone (3 to 10 ng/mL).
Figures 7A, 7B:
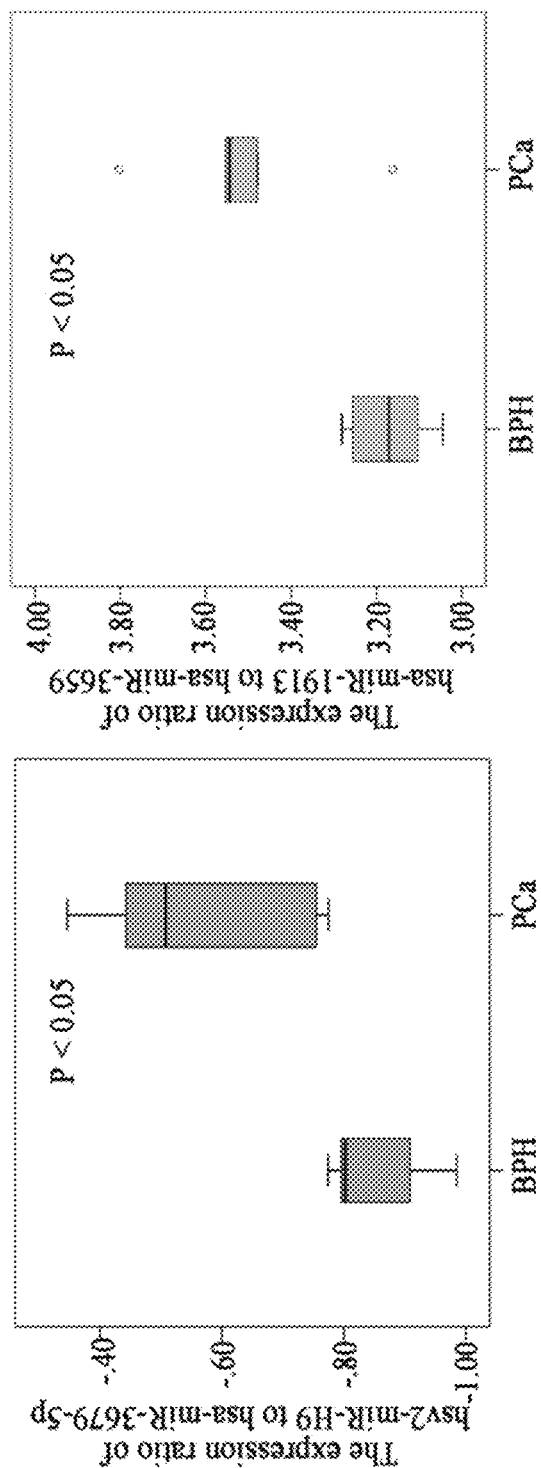
FIGS. 7A and 7B show graphs illustrating the statistical significance of difference in diagnostic scores between the group of benign prostatic hyperplasia subjects (BPH) and the group of prostate cancer subjects (PCa) as described in Examples 3 and 4 for the group of subjects in the PSA gray zone (3 to 10 ng/mL).
Figure 8B:
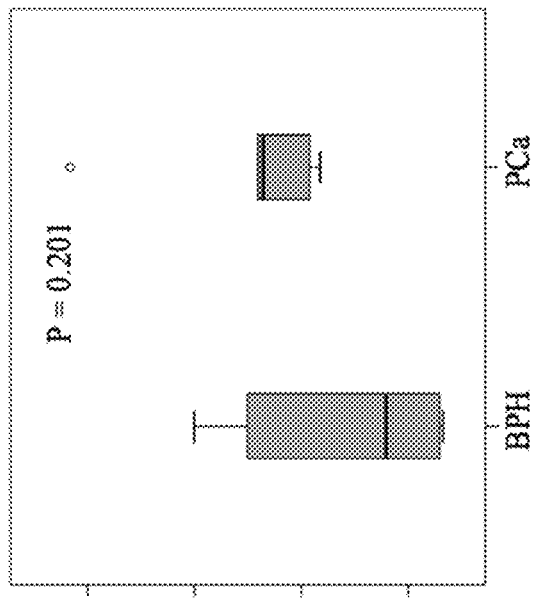
FIGS. 8A and 8B show graphs illustrating the statistical significance of difference in diagnostic scores between the group of benign prostatic hyperplasia subjects (BPH) and the group of prostate cancer subjects (PCa) as described in Examples 5 and 6 for the group of subjects in the PSA gray zone (3 to 10 ng/mL).
Figure 8A:
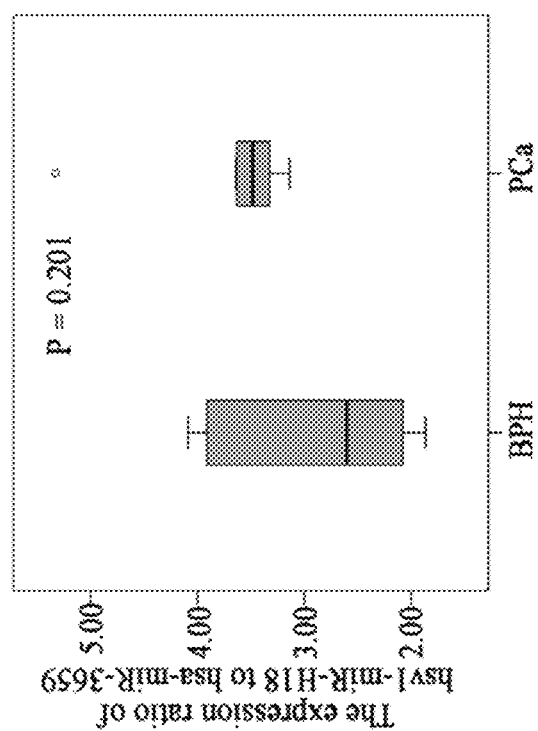
Figures 9A, 9B:
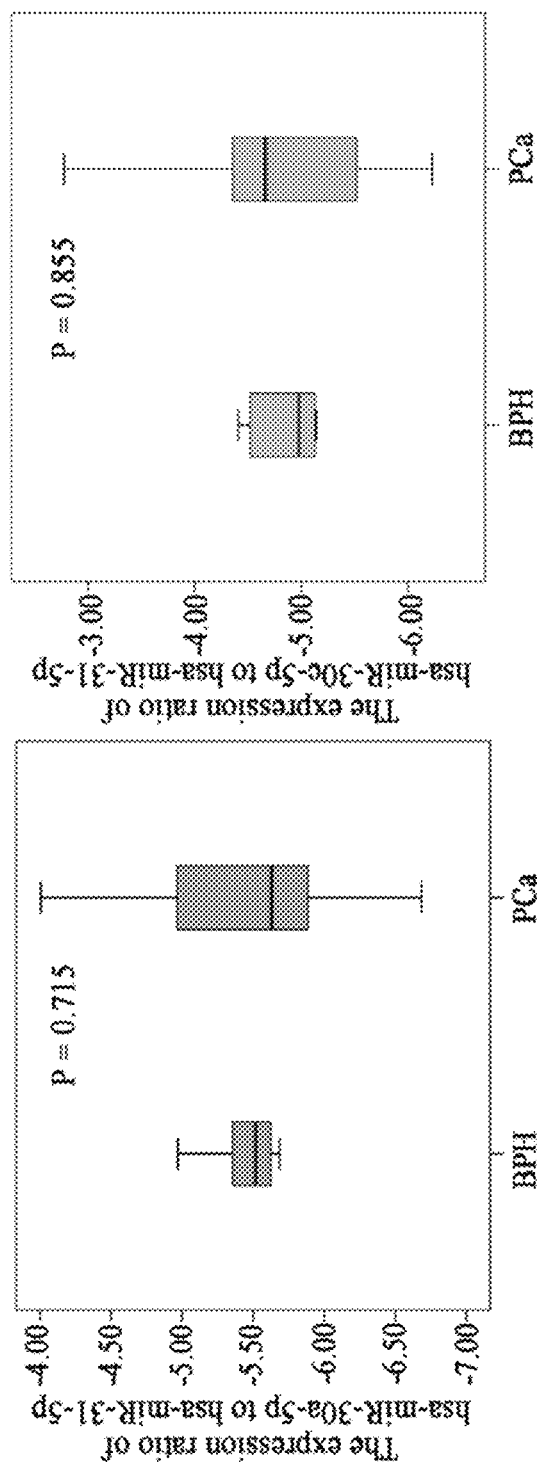
FIGS. 9A and 9B show graphs illustrating the statistical significance of difference in diagnostic scores between the group of benign prostatic hyperplasia subjects (BPH) and the group of prostate cancer subjects (PCa) as described in Comparative Examples 1 and 2 for the group of subjects in the PSA gray zone (3 to 10 ng/mL).
Figure 10:
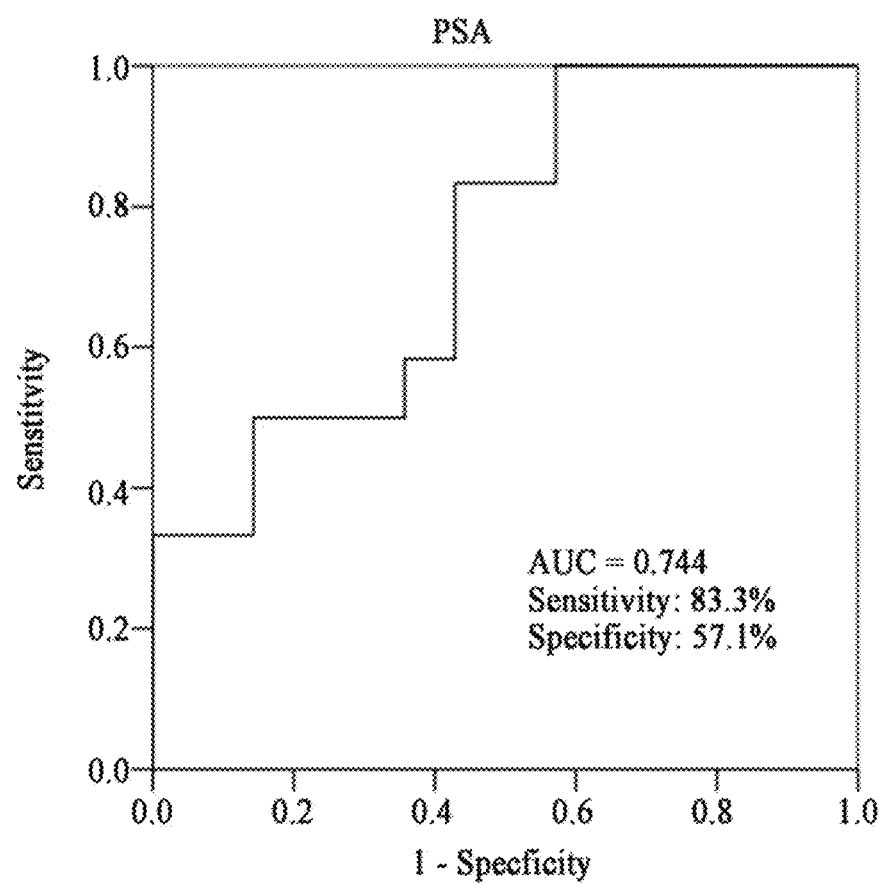
FIG. 10 is a graph illustrating an ROC curve for all the groups of subjects in a PSA test.
Figures 11A, 11B:
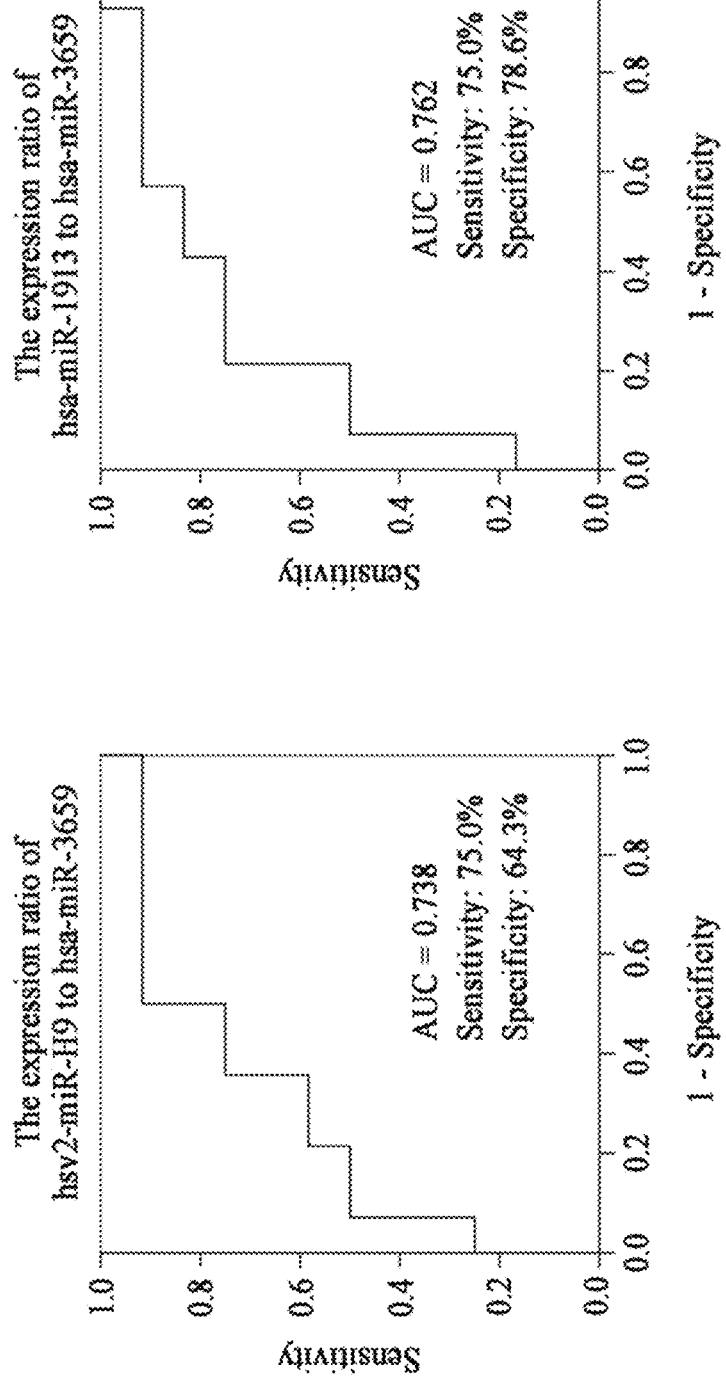
FIGS. 11A and 11B show graphs illustrating an ROC curve for all the groups of subjects as described in Examples 1 and 2.
Figure 12A:
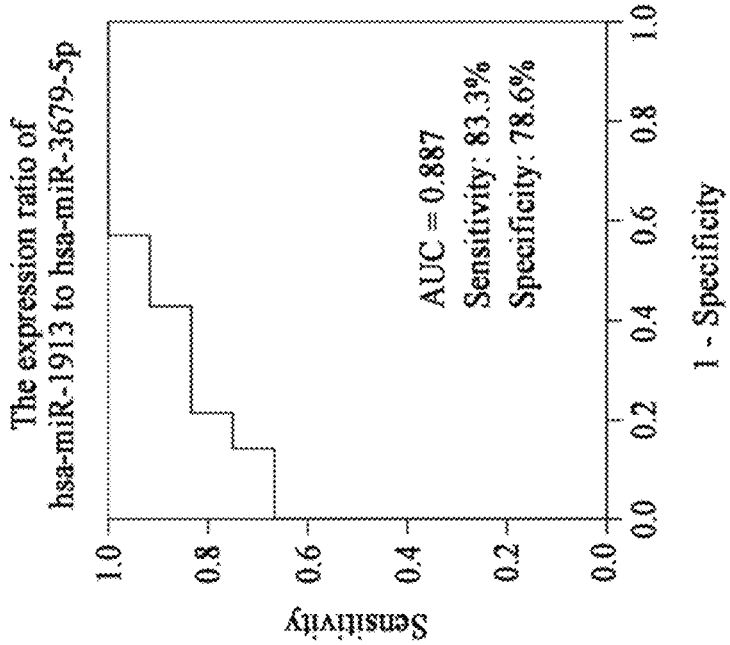
FIGS. 12A and 12B show graphs illustrating an ROC curve for all the groups of subjects as described in Examples 3 and 4.
Figure 12B:
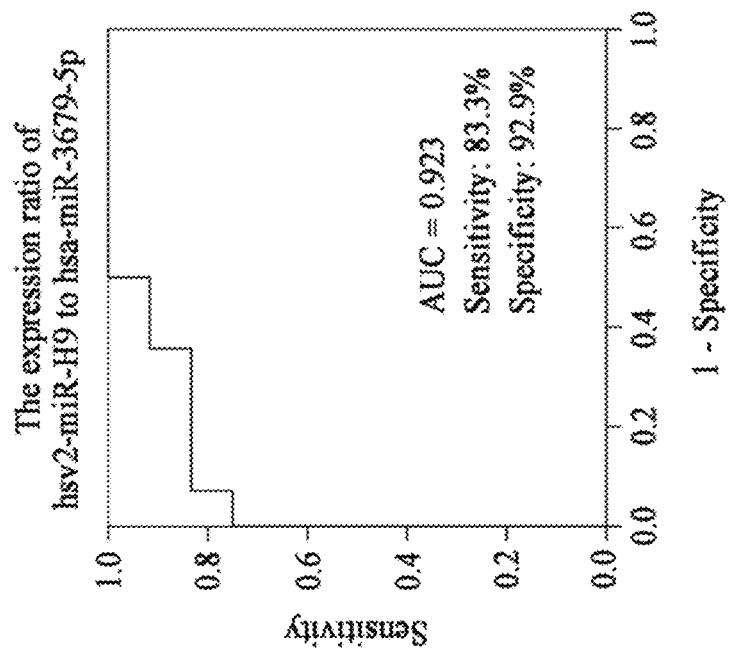
Figure 13B:
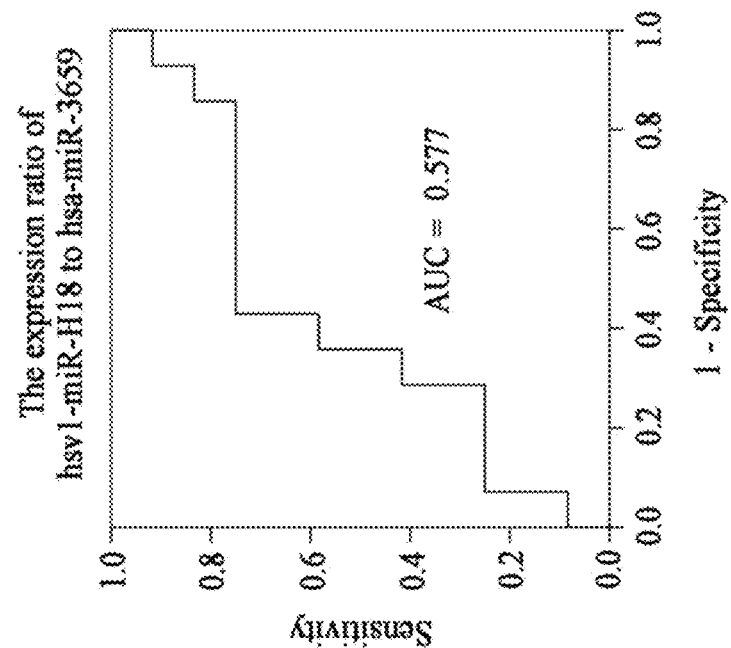
FIGS. 13A and 13B show graphs illustrating an ROC curve for all the groups of subjects as described in Examples 5 and 6.
Figure 13A:
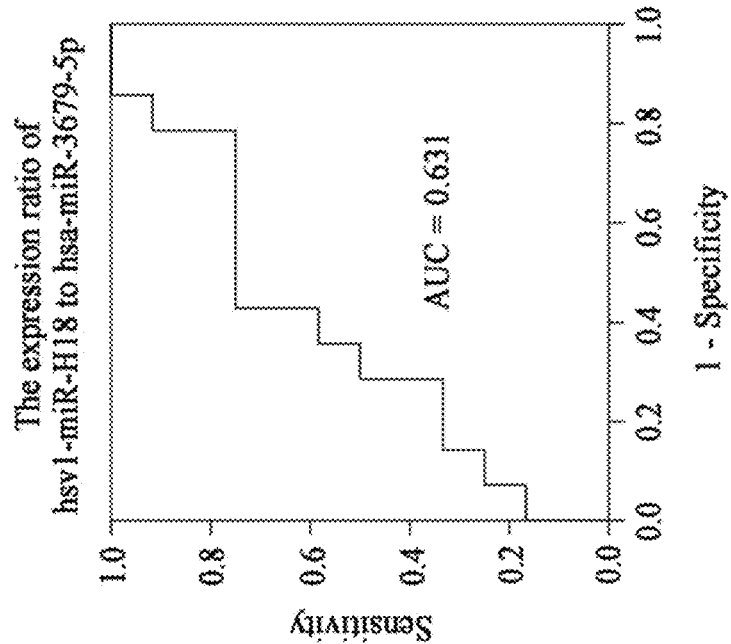
Figures 14A, 14B:
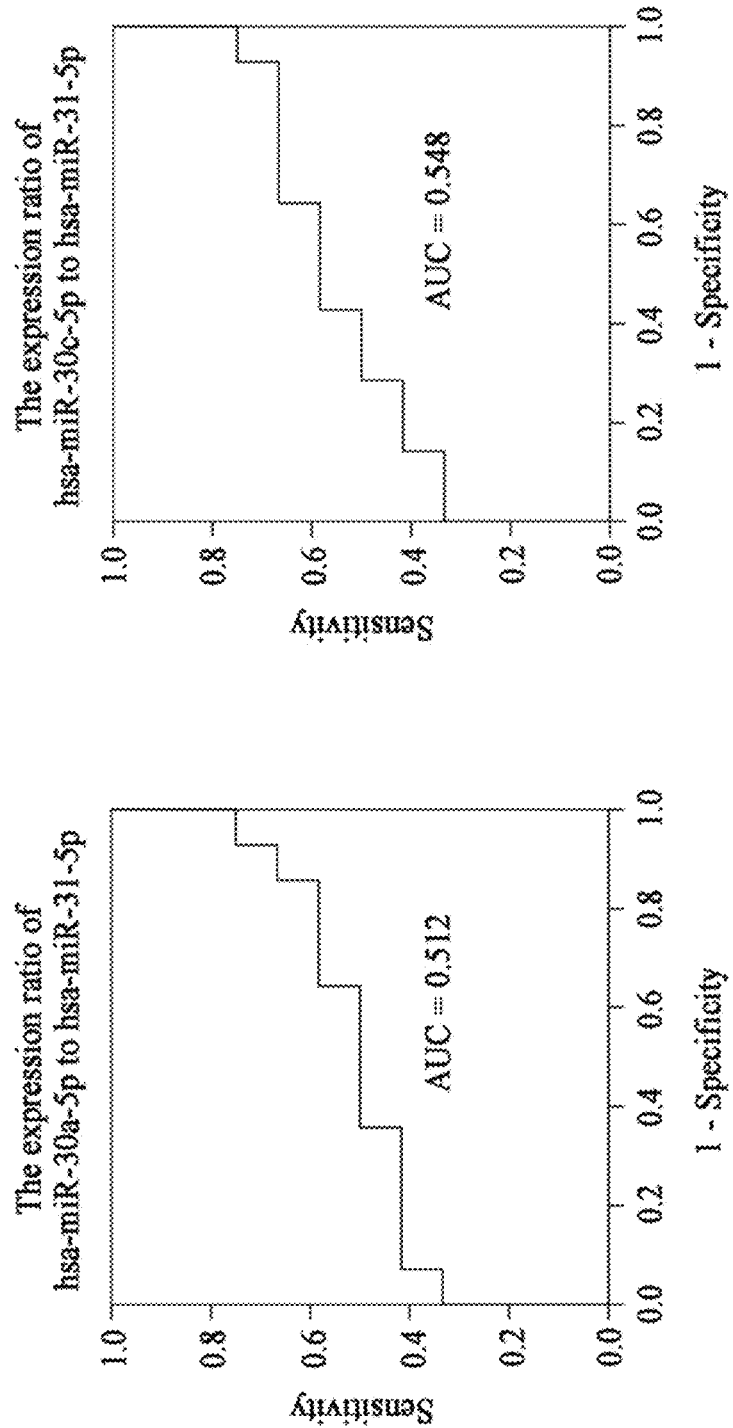
FIGS. 14A and 14B show graphs illustrating an ROC curve for all the groups of subjects as described in Comparative Examples 1 and 2.
Figure 15:
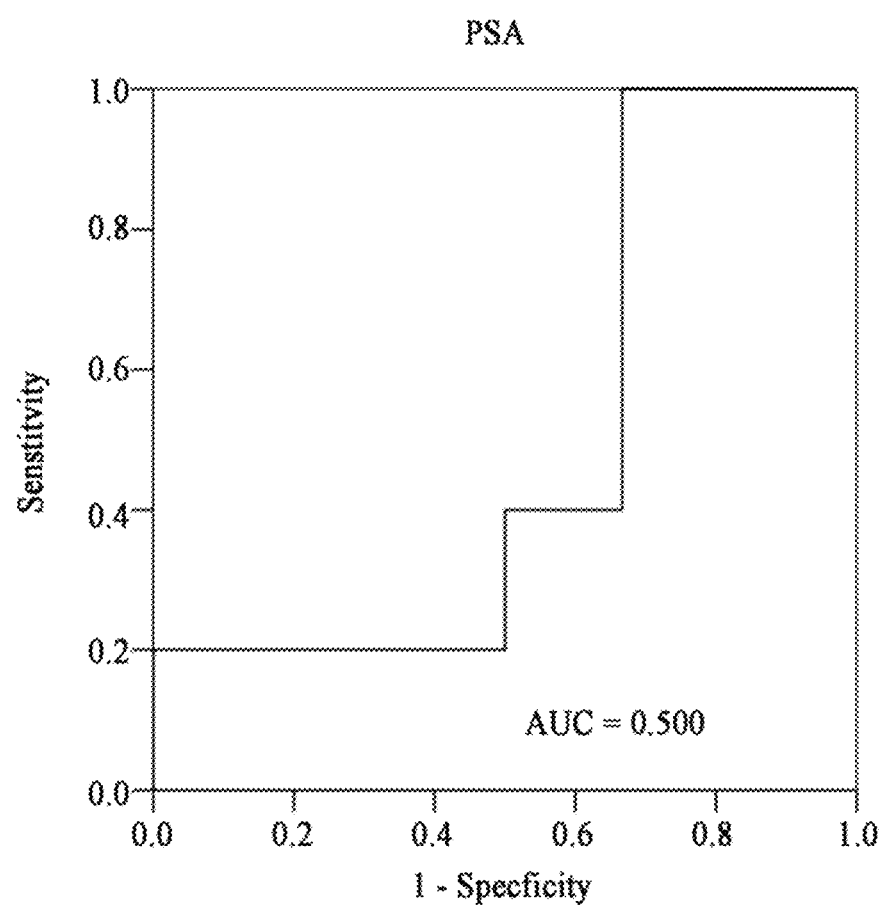
FIG. 15 is a graph illustrating an ROC curve for a group of subjects in a PSA gray zone (3 to 10 ng/mL) in a PSA test. In this case, because the diagnostic performance fell short of the standard, the sensitivity and specificity values are not shown in a separate manner.
Figures 16A, 16B:
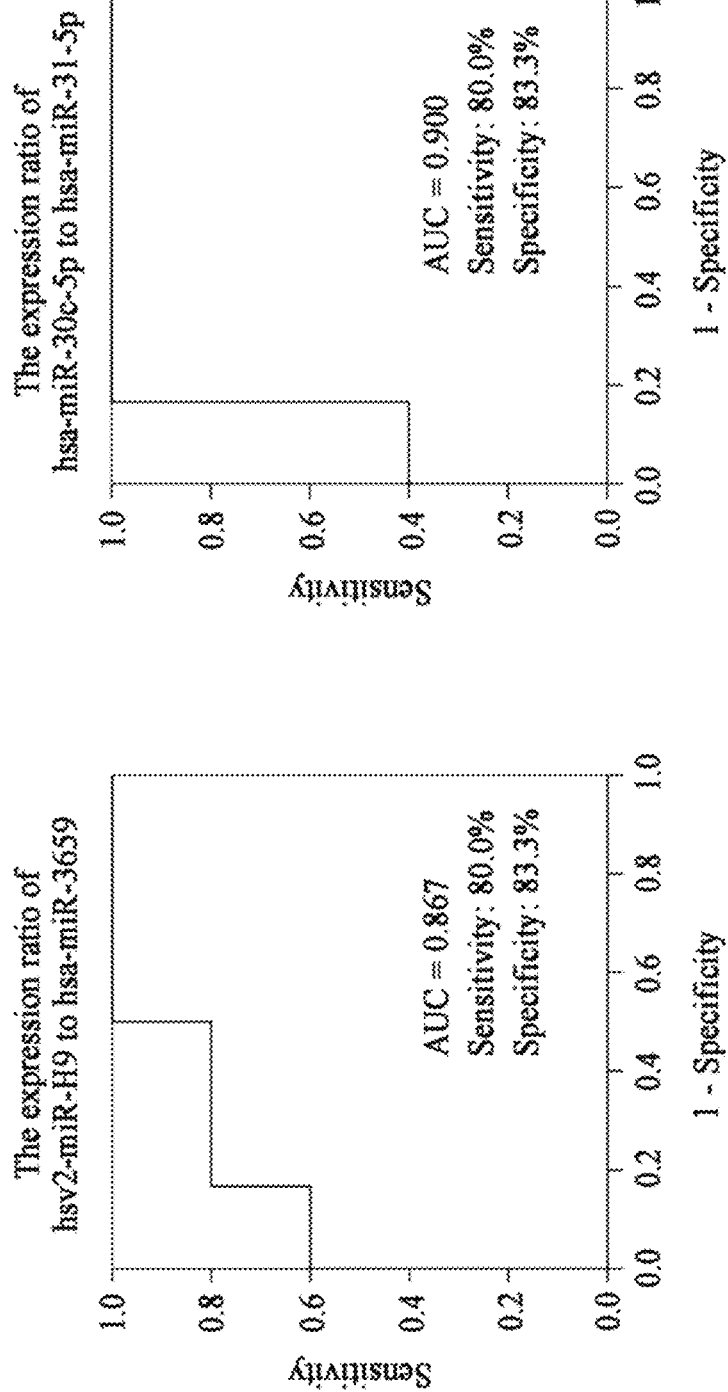
FIGS. 16A and 16B show graphs illustrating an ROC curve for the group of subjects in the PSA gray zone (3 to 10 ng/mL) in Examples 1 and 2.
Figure 17A:
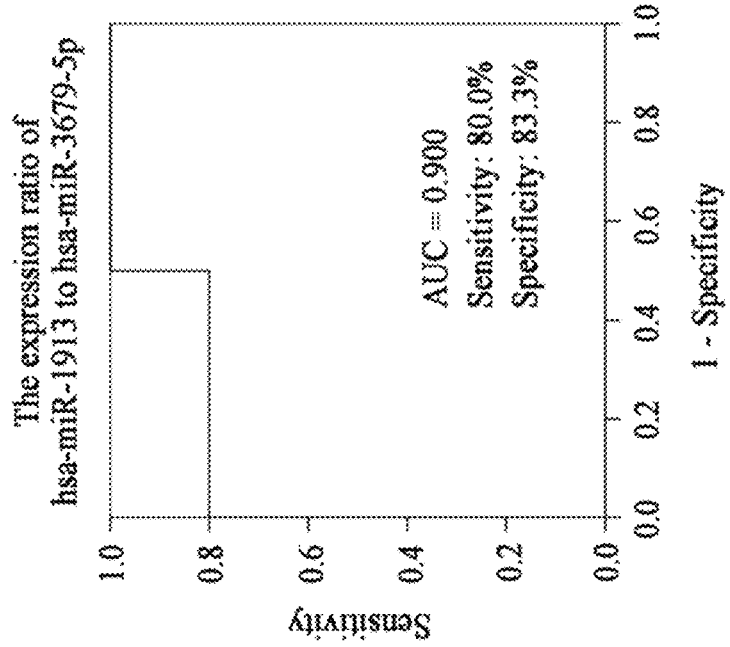
FIGS. 17A and 17B show graphs illustrating an ROC curve for the group of subjects in the PSA gray zone (3 to 10 ng/mL) in Examples 3 and 4.
Figure 17B:
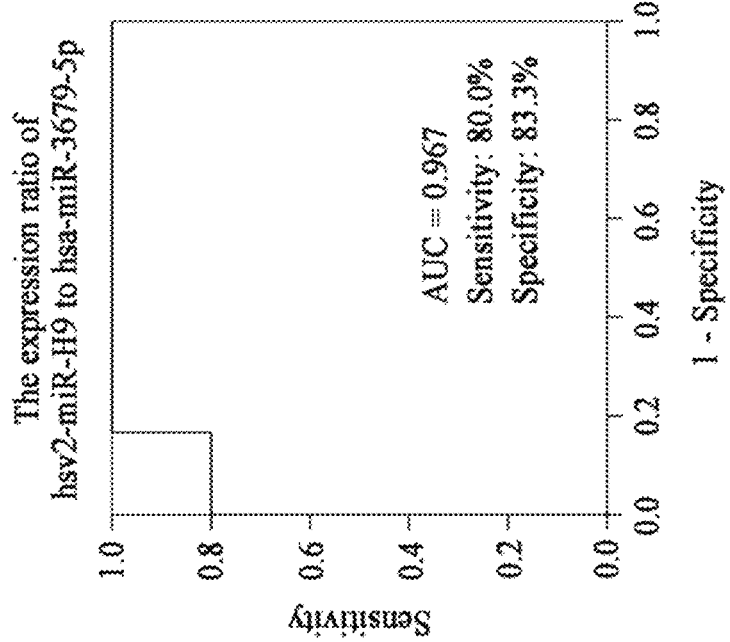
Figures 18A, 18B:
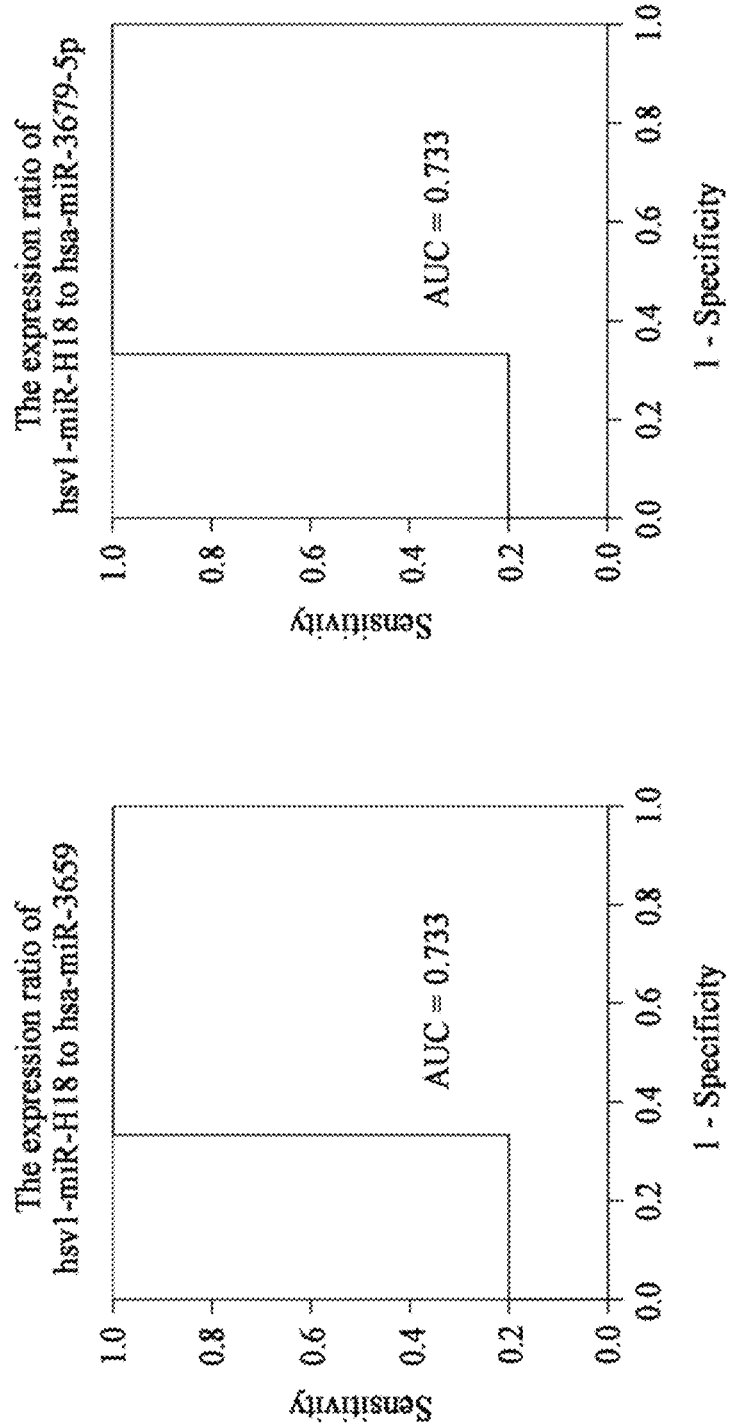
FIGS. 18A and 18B show graphs illustrating an ROC curve for the group of subjects in the PSA gray zone (3 to 10 ng/mL) in Examples 5 and 6.
Figures 19A, 19B:
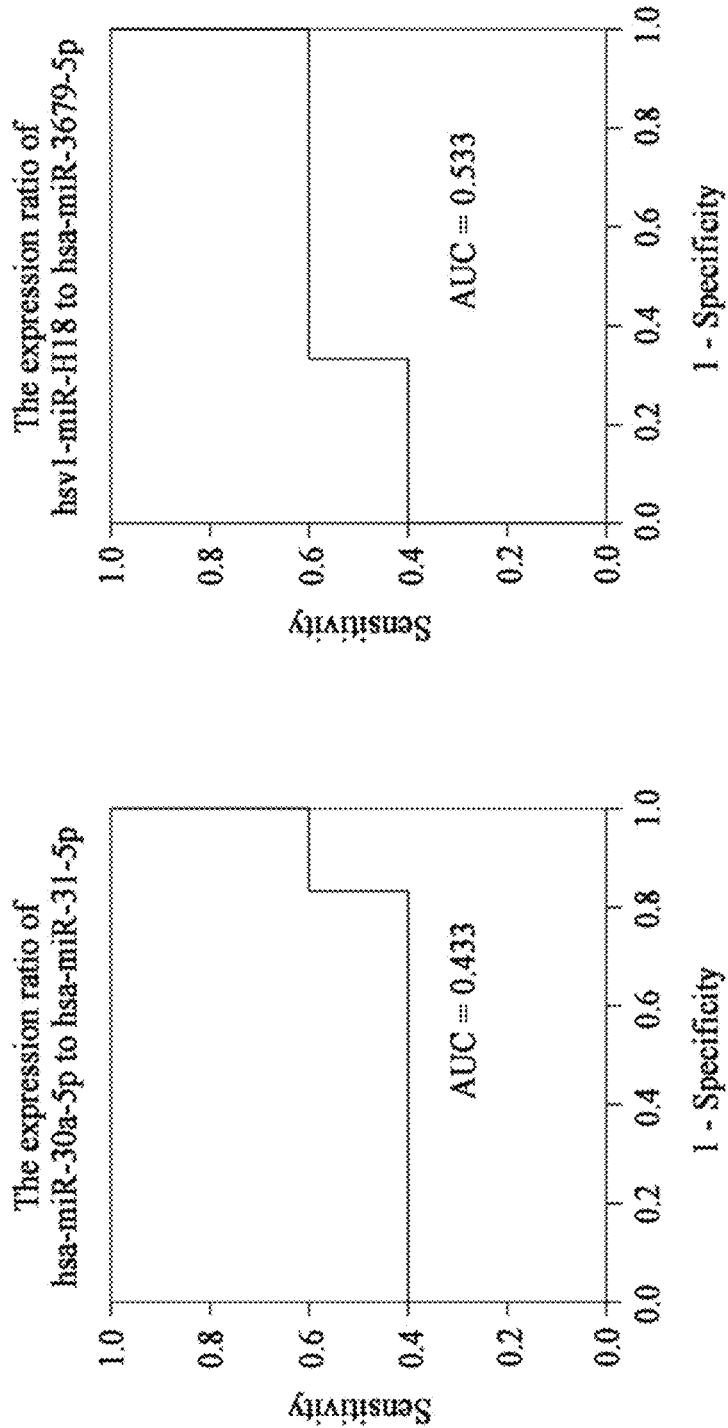
FIGS. 19A and 19B show graphs illustrating an ROC curve for the group of subjects in the PSA gray zone (3 to 10 ng/mL) in Comparative Examples 1 and 2.

Experimental Example 4.1. Statistical Significance of the Diagnostic Score Difference Between Each Group Results of a statistical significance test for the diagnostic score difference between each group for each experimental example are shown in FIGS. 2 to 9. In the case of Example 1 to Example 4, a diagnostic score of the subjects with prostate cancer is significantly higher compared to the BPH subjects (FIGS. 2 to 3, and FIGS. 6 to 7). Even when the subjects are limited to the PSA gray zone, the statistical significance was shown to remain high. On the other hand, in the case of Example 5 and Example 6, there is no significance difference between the diagnostic score of the subjects with prostate cancer and the BPH subjects (FIGS. 4 and 8). As described above, the results might be interpreted that the effect of endogenous factor reflected in a second value does not have a significant correlation with the effect of endogenous effect reflected in a first value, in the Example 5 and 6. It also shows that it does not mean that all of the values can be used as a second value even if the value is 1) obtained from miRNA derived from extracellular vesicles, and 2) reflecting an information associated with the prostate cancer. In the case of Comparative example 1 and Comparative example 2, there is no significance difference between the diagnostic score of the subjects with prostate cancer and the BPH subjects (FIGS. 5 and 9).

Experimental Example 4.2. Receiver Operating Characteristic (ROC) Curves of Diagnostic Scores ROC curves of diagnostic scores for each example are shown in FIGS. 10 to 19. The information of optimal sensitivity, optimal specificity, and area under the curve (AUC) is also shown in the figures. As expected from the results of Experimental Example 4.1, in the case of Example 1 to Example 4, all subjects in the whole group and the subjects in the PSA gray zone show sufficiently high values for AUC, sensitivity, and specificity values. On the other hand, the cases of Example 5, Example 6, Comparative example 1, and Comparative example 2 showed p-value and AUC values below the standard, which is indicating that they were unsuitable for diagnosis of prostate cancer.

What is claimed is:

1. A method for identifying and treating prostate cancer in a subject, the method comprising:
   determining the amount of hsa-miR-3659 or hsa-miR-3679 in a urine sample obtained from the subject; and
   determining the amount of hsv2-miR-H9-5p or hsa-miR-1913 in the urine sample, wherein the ratio of the amount of hsa-miR-3659 or hsa-miR-3679 relative to the amount of hsv2-miR-H9-5p or hsa-miR-1913 is indicative of the presence or absence of prostate cancer in the subject; and
   if the ratio indicates that prostate cancer is present in the subject, performing a biopsy on the subject.

2. The method according to claim 1, wherein determining the amount of hsa-miR-3659 or hsa-miR-3679 comprises:
   synthesizing a first cDNA of hsa-miR-3659 or hsa-miR-3679 from the urine sample;
   amplifying the first cDNA by polymerase chain reaction using a first primer,
      wherein when the first cDNA is synthesized from hsa-miR-3659, the first primer has a sequence of SEQ ID NO 1,
      wherein when the first cDNA is synthesized from hsa-miR-3679, the first primer has a sequence of SEQ ID NO 2; and
   determining the amount of hsa-miR-3659 or hsa-miR-3679 from the amplified first cDNA.

3. The method according to claim 1, wherein determining the amount of hsv2-miR-H9-5p or hsa-miR-1913 comprises:
   synthesizing a second cDNA of hsv2-miR-H9-5p or hsa-miR-1913 in the urine sample;
   amplifying the second cDNA by polymerase chain reaction using a second primer,
      wherein when the second cDNA is synthesized from hsv2-miR-H9-5p, and the second primer has a sequence of SEQ ID NO 3,
      wherein when the second cDNA is synthesized from hsa-miR-1913, and the second primer has a sequence of SEQ ID NO 5; and
   determining the amount of hsa-miR-3659 or hsa-miR-3679 from the amplified second cDNA.

4. The method according to claim 1, wherein the determining further comprises:

synthesizing a cDNA of the hsa-miR-3659 or hsa-miR-3679 in the sample;

amplifying the cDNA by polymerase chain reaction using a first primer, wherein the first primer has the nucleic acid sequence of SEQ ID NO: 1 or 2; and determining the amount of the amplification product of the cDNA of the hsa-miR-3659 or hsa-miR-3679.

5. The method according to claim 4, further comprising:

synthesizing a cDNA of the hsv2-miR-H9-5p or hsa-miR-1913 in the sample;

amplifying the cDNA by polymerase chain reaction using a second primer, wherein the second primer has a sequence including a homologous sequence to the second target or a complementary sequence to the hsv2-miR-H9-5p or hsa-miR-1913; and determining the amount of the amplification product of the cDNA of the hsa-miR-3659 or hsa-miR-3679.

6. The method according to claim 5, wherein the second primer has a sequence selected from SEQ ID NOs.: 3 and 5.

\* \* \* \* \*